US011237126B2

(12) United States Patent
Niemeyer et al.

(10) Patent No.: US 11,237,126 B2
(45) Date of Patent: Feb. 1, 2022

(54) FLUID SENSOR, SYSTEM FOR TESTING A SAMPLE AND PROCESS

(71) Applicant: BOEHRINGER INGELHEIM VETMEDICA GMBH, Ingelheim am Rhein (DE)

(72) Inventors: Axel Niemeyer, Bielefeld (DE); Guenter Bruckmann, Wuerselen (DE); Jakob Mustafa, Herzogenrath (DE)

(73) Assignee: BOEHRINGER INGELHEIM VETMEDICA GMBH, Ingelheim am Rhein (DE)

( * ) Notice: Subject to any disclaimer, the term of this patent is extended or adjusted under 35 U.S.C. 154(b) by 124 days.

(21) Appl. No.: 16/586,180

(22) Filed: Sep. 27, 2019

(65) Prior Publication Data

US 2020/0103362 A1 Apr. 2, 2020

(30) Foreign Application Priority Data

Oct. 1, 2018 (EP) .................................. 18197996

(51) Int. Cl.
*G01N 27/00* (2006.01)
*G01N 27/22* (2006.01)
(Continued)

(52) U.S. Cl.
CPC ......... *G01N 27/228* (2013.01); *C12Q 1/6806* (2013.01); *C12Q 1/6874* (2013.01); *G01D 5/24* (2013.01); *C12Q 2565/60* (2013.01)

(58) Field of Classification Search
CPC ............ C12Q 1/6869; C12Q 2535/101; C12Q 1/6806; C12Q 1/6874; C12Q 2565/60; B01J 2219/00353; B01J 2219/0036; B01J 2219/00364; B01J 2219/00608; B01J 2219/0061; B01J 2219/00612; B01J 2219/00619; B01J 2219/00626;
(Continued)

(56) References Cited

U.S. PATENT DOCUMENTS 3,753,092 A * 8/1973 Ludlow .............. G01R 27/2635
324/663
5,096,669 A 3/1992 Lauks et al.
(Continued)

FOREIGN PATENT DOCUMENTS

DE 102010013812 A1 10/2011

*Primary Examiner* — Vincent Q Nguyen
(74) *Attorney, Agent, or Firm* — David S. Safran; Roberts Calderon Safran & Cole, P.C.

(57) ABSTRACT

A fluid sensor for detecting a content change, in particular a liquid front, in a sensor portion of a fluid system, wherein the fluid sensor includes at least one sensor electrode, the sensor electrode having an electrode potential and a capacitive behavior, the sensor electrode thus being capable to store electrical energy in an electrical field formed by the sensor electrode when being charged, causing the electrode potential to change accordingly, a capacitance value of the sensor electrode varies when the content changes, the fluid sensor includes evaluation electronics, the evaluation electronics including a unidirectional electrical device (UED), and an AC source, the AC source is coupled via the UED to the sensor electrode to charge the sensor electrode, and the evaluation electronics include a discharge path coupled to the sensor electrode for discharging the sensor electrode.

19 Claims, 9 Drawing Sheets

(51) Int. Cl.
*C12Q 1/6806* (2018.01)
*C12Q 1/6874* (2018.01)
*G01D 5/24* (2006.01)

(58) Field of Classification Search
CPC .... B01J 2219/00637; B01J 2219/00653; B01J 2219/00657; B01J 2219/00659; B01L 2200/0673; B01L 2200/10; B01L 2300/0864; B01L 2300/0867; B01L 2400/0421; B01L 2400/0487; B01L 3/0293; B01L 3/502715; B01L 3/502784; B01L 7/52; F15C 5/00; G01F 1/662; G01F 1/667; G01F 23/266; G01N 1/14; G01N 27/223; G01N 27/228; G01N 27/44743; G01N 27/44769; G01N 35/08; G01R 27/2635
USPC .................. 324/453, 658, 663, 717; 204/412
See application file for complete search history.

(56) References Cited

U.S. PATENT DOCUMENTS

| | | |
|---|---|---|
| 7,838,261 B2 | 11/2010 | Gumbrecht et al. |
| 8,225,654 B2 | 7/2012 | Muerset |
| 8,950,424 B2 | 2/2015 | Weber et al. |
| 9,110,044 B2 | 8/2015 | Gumbrecht et al. |
| 2004/0173456 A1 | 9/2004 | Boos et al. |
| 2006/0084069 A1* | 4/2006 | Chan .................. G01N 21/6454 435/6.15 |
| 2008/0207461 A1 | 8/2008 | Ermantraut et al. |
| 2016/0369790 A1* | 12/2016 | Yavorsky ................ F04B 19/22 |

\* cited by examiner

FLUID SENSOR, SYSTEM FOR TESTING A SAMPLE AND PROCESS

BACKGROUND OF THE INVENTION

Field of the Invention

The present invention relates to a fluid sensor, an analysis system and a process.

Preferably, the present invention relates to or deals with analyzing and testing a sample, in particular from a human or animal, particularly preferably for analytics and diagnostics, for example with regard to the presence of diseases and/or pathogens and/or for determining blood counts, antibodies, hormones, steroids or the like. Therefore, the present invention is in particular within the field of bioanalytics. A food sample, environmental sample or another sample may optionally also be tested, in particular for environmental analytics or food safety and/or for detecting other substances.

Preferably, at least one analyte (target analyte) of a sample can be determined, identified or detected. In particular, the sample can be tested for qualitatively or quantitatively determining at least one analyte, for example in order for it to be possible to detect or identify a disease and/or pathogen.

Within the meaning of the present invention, analytes are in particular nucleic-acid sequences, in particular DNA sequences and/or RNA sequences, and/or proteins, in particular antigens and/or antibodies. In particular, by means of the present invention, nucleic-acid sequences can be determined, identified or detected as analytes of a sample, and/or proteins can be determined, identified or detected as analytes of the sample. More particularly preferably, the present invention deals with systems, devices and other apparatuses for carrying out a nucleic-acid assay for detecting or identifying a nucleic-acid sequence and/or a protein assay for detecting or identifying a protein.

The present invention deals in particular with what are known as point-of-care systems, i.e. in particular with mobile systems, devices and other apparatuses, and deals with methods for carrying out tests on a sample at the sampling site and/or independently and/or away from a central laboratory or the like. Preferably, point-of-care systems can be operated autonomously of and/or independently from a mains network for supplying electrical power.

Description of the Related Art

U.S. Pat. No. 5,096,669 discloses a point-of-care system for testing a biological sample, in particular a blood sample. The system includes a single-use cartridge and an analysis device. Once the sample has been received, the cartridge is inserted into the analysis device in order to carry out the test. The cartridge includes a microfluidic system and a sensor apparatus including electrodes, which apparatus is calibrated by means of a calibration liquid and is then used to test the sample.

Furthermore, International Patent Application Publication WO 2006/125767 A1 and corresponding U.S. Pat. No. 9,110,044 B2 disclose a point-of-care system for integrated and automated DNA or protein analysis, including a single-use cartridge and an analysis device for fully automatically processing and evaluating molecular-diagnostic analyses using the single-use cartridge. The cartridge is designed to receive a sample, in particular blood, and in particular allows cell disruption, PCR and detection of PCR amplification products, which are bonded to capture molecules and provided with a label enzyme, in order for it to be possible to detect bonded PCR amplification products or nucleic sequences as target analytes in what is known as a redox cycling process. A capacitative level sensor is disclosed having two plates. However, there is no hint regarding how to achieve a more reliable detection or less complex construction.

German Patent DE 100 58 394 C1 and corresponding U.S. Pat. No. 7,838,261 disclose a method for testing a sample using a reaction array including at least two reaction compartments for receiving substances that react with one another, the reaction compartments being interconnected by means of a supply space. In order to measure the substances, an exchange of substances and thus chemical crosstalk between the individual reaction compartments is prevented by lowering a sensor cover. In this way, the detection sensitivity of the method is increased.

European Patent Application EP 2 305 383 B1 and corresponding U.S. Patent Application Publication 2008/0207461 A1 discloses an instrument for carrying out and analyzing microarray experiments. In particular, this document discloses carrying out microarray experiments in parallel in order to detect specific interactions between probe molecules and target molecules in a microtiter plate. In this case, probes in the form of a substance library are provided on carriers, and therefore a sample can be simultaneously analyzed on a plurality of probes in parallel. In the context of microarray experiments of this kind, it is also disclosed that a desired operating mode can be specified for a processing apparatus externally, in particular by a user. However, there is no hint regarding any sensor portion through which a sample can flow, and no hint how to improve detecting a content change within such sensor portion.

"Multielectrode capacitors" In Larry K. Baxter: "Capacitive Sensors: Design and Applications", 31 Aug. 1996, Wiley-IEEE Press discloses in chapter 2.3.2 "Multielectrode capacitors" an air spaced capacitor having three electrodes, one of which is connected to ground for shielding. The chapter relates to multielectrode capacitors, i.e. having more than two nodes, and there is no hint regarding connecting capacitor electrodes. Moreover, the capacitor electrodes are shielded in their entirely and, thus, are not suitable for sensing purposes.

SUMMARY OF THE INVENTION

Problem addressed by the present invention is to provide a fluid sensor, an analysis system and a process for more accurately or reliably testing a sample.

The above problem is achieved by the fluid sensor according to claim 1, an analysis system according to claim 14 or a process according to claim 15. Advantageous embodiments are subject of the dependent claims.

The present invention in a first aspect relates to a fluid sensor for detecting a content change, in particular a liquid front, in a sensor portion of a fluid system. Such fluid system can form part of a cartridge for receiving a sample, the cartridge including a fluid system for guiding the sample. This fluid system can have a sensor portion formed by a part of this fluid system through which a liquid can flow. If this sensor portion is empty or filled with gas in an initial state, liquid like a liquid sample entering the sensor portion can cause a detectable content change of the sensor portion.

The fluid sensor according to the present invention preferably detects said content change based on a change of an electrical parameter of the content of the sensor portion. Particularly preferably, the fluid sensor is a capacitive fluid sensor being configured or able to detect a change in a (relative) permittivity of the content of the sensor portion. For example, if a liquid front enters the sensor portion and, thus, replaces a former content of the sensor portion which had a different permittivity, this changed permittivity can be detected and interpreted as a content change.

The fluid sensor includes at least one sensor electrode, the sensor electrode having an electrode potential. An electrode potential according to the present invention is an electrical potential in the sense that a difference between the electrode potential and a different potential results in a voltage. A difference between the electrode potential and ground in the following is referred to as electrode voltage. In the following, the terms electrode potential and electrode voltage are used interchangeably, and, thus, the term electrode potential can be replaced with the term electrode voltage or vice versa. In the following, more generally, the present invention generally is described using potentials while the term "potential" generally can be replaced with the term "voltage" or vice versa.

Further, the sensor electrode according to the present invention has a capacitive behavior. This means that the sensor electrode somehow forms a capacitor. This capacitor is configured or arranged such that the content change in the sensor portion is capable of changing electrical properties of the capacitor formed with or by the sensor electrode.

Due to the capacitive behavior, the sensor electrode is capable of storing electrical energy in an electrical field formed by the sensor electrode.

Electrical energy is stored in the electrical field when the sensor electrode is charged. Charging in the sense of the present invention means that charge carriers like electrons are added to or removed from the sensor electrode. This causes the electrode potential to change accordingly.

The sensor electrode has a capacitance value. This capacitance value can be specified in the dimension pF. The degree of change in electrode potential compared to the number of charge carriers is defined by the capacitance value.

The capacitance value of the sensor electrode varies when the content of the sensor portion changes to one with different permittivity. For that purpose, the sensor portion can, in a use-arrangement, be arranged in the surrounding area of the sensor electrode such that the capacitance value depends on the permittivity of the content of the sensor portion and a content change causing a change of permittivity, thus, causes the capacitance value to change. This change preferably is determined by the fluid sensor and/or is used by the fluid sensor to generate an output signal and/or measurement result.

The fluid sensor according to the present invention includes evaluation electronics. Those evaluation electronics preferably is configured to detect a change in electrical properties of the sensor portion when a content change takes place using the sensor electrode.

The evaluation electronics according to a first aspect of the present invention includes a uni-directional electrical device, for which in the following the abbreviation UED is used. UEDs are configured to enable current flow in one direction and block current flow in a different, in particular opposite, direction. The most common and preferred UED is a diode. Other examples for UEDs are thyristors or electrical circuits resulting in a similar behavior. For example, a switch can be used as UED when switched accordingly.

For further properties of UEDs, reference is made to the Wikipedia articles as regards diodes under https://en.wikipedia.org/wiki/diode and rectifier under https://en.wikipedia.org/wiki/rectifier.

Preferably, UEDs generally have an essentially diode like behavior. Alternatively, or additionally to a diode, the UED can be realized by a circuit having a substantially equivalent behavior.

UEDs preferably automatically and/or without external control enable current flow in one direction and block current flow in the opposite direction between two ports. In particular, a voltage across those ports controls whether the UED opens or blocks.

A UED might have a threshold voltage which has to be reached or exceeded for starting significant current flow in the direction in which the UED enables current flow.

A UED might have negligible parasitic or intrinsic currents regardless of or in addition to the behavior discussed above.

With other words, the function of a UED to enable current flow in one direction and block current flow in the other direction preferably is essentially independent on any external control and/or an intrinsic function of the UED.

Preferably, a voltage across the UED or ports thereof with a first, in particular positive, sign, enables current flow (e.g., in one direction and/or automatically) while a voltage across the UED or ports thereof having an opposite, in particular negative, sign causes blocking current flow (e.g., in the different/opposite direction and/or automatically).

In case a UED is realized by a device having at least one control port, like a thyristor, preferably the basic function of the UED remains unchained between two ports being provided in addition to the control port. That is, such device (automatically) enables current flow in one direction (only) and blocks current flow in the opposite direction between the two ports, in particular either when controlled via the control port or regardless thereof.

Referring to a thyristor as UED, for example, in addition to the basic function described above, in the flow direction in which the UED enables current flow, a minimum voltage for starting conduction can be changed by means of the control port, while the current flow in the opposite direction always is (automatically) blocked.

Referring to a transistor as UED, such transistor is configured to (automatically) conduct current only in one direction and (automatically) block current in the other direction. In particular, a field effect transistor, referred to as FET, in particular a MOSFET, can be used which is connected such that (automatically) current flow in one direction is enabled while in the other (opposite) direction the current flow is blocked.

One example for an UED formed by a circuit having a diode like behavior is an (enhancement mode) FET or MOSFET which has its gate connected with its source or drain such that its characteristics become similar to those of diode, namely enabling current flow in one direction and blocking current flow in a different/opposite direction (automatically).

In such case, while a FET or MOSFET as such has at least three or, in consideration of the substrate contact, four ports, the UED realized by such MOSFET or different transistor is reduced to two ports, e.g., by connecting the gate to source accordingly. Across those two ports, the UED realized with the FET or MOSFET in the end preferably has a diode like behavior.

In case a bipolar transistor is used, the base can be connected with emitter or collector such that a behavior of an UED or diode is achieved.

Generally speaking, an UED preferably has at least or exactly two ports across which the UED (automatically) enables current flowing only from one port to the other and blocks current in the opposite direction which can be controlled by a voltage across those ports. This further preferably is regardless of any further control ports at least in the configuration in use. The UED preferably is configured to enable this function without external control or without change in state by means of external control.

A UED can optionally be or be called a rectifier device or vice versa. This is due to the fact that a rectifying device or rectifier (circuit) acts as a unidirectional electronic device transmitting current only in one direction and blocking it in the other direction, thus, causing an AC current to result in a DC current flowing merely in one direction. This typically results in a unidirectional current which might or might not be more or less pulsating.

Alternatively, or additionally, one can say a UED acts as a unidirectional current valve. Such unidirectional current valve enables current flow in one direction and blocks current flow in an opposite direction, like a check valve, but for a current.

Thus, the terms "UED", rectifier device, and/or unidirectional current valve or unidirectional current check valve preferably are used synonymously and replaceable, while for the sake of conciseness in the following merely UED is used.

The evaluation electronics according to the present invention further include an AC source. An AC source according to the present invention is a voltage and/or current source configured for providing an alternating voltage or current or a combination thereof. The term "AC source" according to the present invention is not limited to sources for providing a sinusoidal voltage or current, but also covers differently shaped voltages or currents like pulsating, square wave, triangular or variably shaped voltages or currents. The AC source according to the present invention preferably provides a pulsating output voltage or current.

The AC source preferably repeats multiple times the same voltage or current pattern. Particularly preferably the (respective) pattern starts with a voltage or current pulse followed by a phase where the AC source provides no current or ground or a reference voltage, preferably over a longer time span than that of the pulse.

The AC source is coupled via the UED to the sensor electrode such that the sensor electrode can be charged using the AC source. The UED has at least two ports, where the UED is configured to enable current flow from the first port of the UED to the second port or to UED while current flow from the second port of the UED back to the first port of the UED is blocked. Accordingly, it is preferred that the AC source is coupled to the first port of the UED and the sensor electrode is coupled to the second port of the UED such that current can flow from the AC source passing the UED to the sensor electrode, but preferably not back. This results in the sensor electrode to be charged, i.e. the electrode potential to be changed by adding or removing charge carriers to or from the sensor electrode.

Moreover, the evaluation electronics according to the present invention preferably includes a discharge path coupled to the sensor electrode for discharging a sensor electrode. The discharge path preferably is distinct from the UED and the AC source. The discharge path enables charge carriers to be removed from the sensor electrode, e.g. by coupling of the sensor electrode to ground or a reference potential.

The discharge path preferably includes at least one impedance for limiting a discharge current and/or is not an electrical short. The discharge path preferably is configured to discharge the sensor electrode continuously over a period of time.

Alternatively, or additionally, the evaluation electronics includes an energy storage for storing electrical energy, preferably a capacitor, which is or can be coupled with the sensor electrode such that charge from the sensor electrode is shared with said energy storage. The sensor electrode being coupled with the energy storage causes charge balancing between the sensor electrode and the energy storage at least to some extent.

The energy storage preferably is an integrating capacitor, integrating (at least to some extend) the potential of the sensor electrode. The evaluation electronics preferably is configured such that the voltage of the integrating capacitor depends on the capacitance value of the sensor electrode. A change in the capacitance value can be used to detect or interpreted as content change of the sensor portion.

While known evaluation electronics typically demand for switches to charge and discharge a sensor electrode and to measure properties of the charge and discharge behavior or to couple capacitors for deriving a measurement result, the fluid sensor of the present invention does not demand for such switches but is realized using an UED which does not need to or cannot be controlled externally, resulting in a resource saving solution with a small device count (bill of material count).

Charging the sensor electrode with the AC source via the UED, and afterwards discharging the sensor electrode via the discharge path causes a discharge process having a discharge curve and/or sharing charge of the sensor electrode with the charge carrier storage causes a resulting potential which can be used or interpreted to detect the capacitance or capacitance value of the sensor electrode and/or the content change, which has been found to work well despite the comparatively low complexity.

Particularly preferably, the evaluation electronics includes both a discharge path and the energy storage. The discharge path can include the energy storage. With other words, the energy storage preferably forms part of the discharge path.

Further preferably, the energy storage can be charged via the discharge path or a part thereof. In particular, a first coupling element—preferably an impedance, in particular a resistor—of the discharge path couples the sensor electrode with the energy storage. Accordingly, the UED and/or the sensor electrode is/are separated from the energy storage by means of this first coupling element and/or the energy storage can be charged with charge carriers from the sensor electrode being transferred to the energy storage via the first coupling element.

Alternatively, or additionally, a (second) coupling element—preferably an impedance, in particular a resistor—couples the first coupling element and/or the energy storage to a sink, reference potential, and/or ground. The (second) coupling element allows the sensor electrode and/or the energy storage to be discharged, preferably continuously. Due to this discharge, use of a switch for coupling the sensor electrode to the energy storage or for discharging the energy storage can be avoided.

In one preferred aspect, the evaluation electronics includes an electrical filter for filtering the course of the electrode potential. Particularly preferably, the evaluation electronics is configured such that the AC source, in particular a period length or frequency of the AC source, and the filter characteristics of the filter are designed such that a content change in the sensor portion enables a significant change of a voltage or current offset at an output of the filter which can be used to form or forms a basis for the output signal and/or the measurement result. The electrical filter can be realized by the energy storage and one or both of the coupling elements.

In a further aspect of the present invention, which can be realized independently as well, the present invention relates to an analysis system for testing in particular a biological sample, the analysis system including an analysis device for receiving a cartridge including a fluid system having a sensor portion, the analysis device including a The fluid sensor according to any one of the proceeding claims for detecting a content change, in particular a liquid font, in the sensor portion.

A further aspect of the present invention, which can be realized independently as well, relates to a process for detecting the content change in the sensor portion of the fluid system with a The fluid sensor according to the present invention. In this aspect, the evaluation electronics of the fluid sensor repeatedly charges the sensor electrode using the AC source via the UED to a predefined electrode potential, and automatically discharges the sensor electrode by means of the discharge path starting from the pre-defined electrode potential approximating the electrode potential to the reference potential each time after charging is finished.

Further, it is preferred that the fluid sensor forms an output signal based on a course of the electrode potential during the course of discharge, the output signal being or forming a basis for a measurement result which is indicative of the capacitance value of the sensor electrode. This measurement result can be used to determine the content change like a fluid front arriving at the sensor portion or passing it.

The fluid sensor preferably measures, in particular as the measurement result, an electrical variable, in particular capacitance or a corresponding gauge, which is dependent on a property, in particular electrical permittivity and/or electrical conductivity and/or electrical permittivity, of the content of the sensor portion. In other words, the fluid sensor can therefore preferably be influenced by the content of the sensor portion such that electrical properties can be changed and detected. This does not mean that the sensor portion content itself has to be conductive or electrically active in another manner, or that electrical current has to flow therethrough, even though this is possible in principle.

If the measurement result changes, it is preferably concluded that there has been a content change in the sensor portion. This conclusion can be drawn by the measurement result being compared with a reference value and the content change being detected if the reference value is exceeded. The actual value is therefore preferably compared with the desired value and/or change and/or with a threshold value.

The fluid sensor preferably forms part of and/or is used to control an analysis device of the analysis system and/or a test therewith.

The term "analysis device" is preferably understood to mean an instrument which is in particular mobile and/or can be used on site, and/or which is designed to chemically, biologically and/or physically test and/or analyze a sample or a component thereof, preferably in and/or by means of a cartridge. In particular, the analysis device controls the pretreatment and/or testing of the sample in the cartridge. For this purpose, the analysis device can act on the cartridge, in particular such that the sample is conveyed, temperature-controlled and/or measured in the cartridge.

The term "cartridge" is preferably understood to mean a structural apparatus or unit designed to receive, to store, to physically, chemically and/or biologically treat and/or prepare and/or to measure a sample, preferably in order to make it possible to detect or determine at least one analyte, in particular a protein and/or a nucleic-acid sequence, of the sample.

A cartridge within the meaning of the present invention preferably includes a fluid system having a plurality of channels, cavities and/or valves for controlling the flow through the channels and/or cavities.

In particular, within the meaning of the present invention, a cartridge is designed to be at least substantially planar and/or card-like, in particular is designed as a (micro)fluidic card and/or is designed as a main body or container that can preferably be closed and/or said cartridge can be inserted and/or plugged into a proposed analysis device when it contains the sample.

The term "test" as used herein preferably means a test procedure, test sequence and/or performing an assay, in particular one, several or all steps for performing an assay to determine one or more analytes of a sample. The steps are preferably realized by or within the analysis system, analysis device and/or cartridge.

An "assay" according to the present invention is preferably an investigative procedure for qualitatively and/or quantitatively measuring, detecting and/or identifying the presence, amount, and/or functional activity of a target entity or analyte of the sample. The analyte can, e.g., be a drug, a biological, chemical and/or biochemical substance, and/or a cell in an organism or organic sample. In particular, the analyte can be a molecule, a nucleic-acid sequence, a DNA, an RNA and/or a protein.

Preferably, the assay according to the present invention is a nucleic-acid assay for detecting or identifying a nucleic-acid sequence and/or a protein assay for detecting or identifying a protein.

An assay, test or test procedure according to the present invention accordingly preferably covers at least one of: controlling actuators of the analysis device like a pump drive, temperature control apparatus, and valve actuators; acting on the cartridge or sample; treating the sample; preparing the sample; performing one or more mixing processes and/or reactions with the sample; conveying the sample; and measuring one or more properties of the sample, particularly with a sensor apparatus of the cartridge. The fluid sensor according to the present invention can be used to initiate, stop, and define and/or change properties of one or more of the previous mentioned measures.

An assay, test or test procedure according to the present invention preferably starts or begins with the analysis device acting on and/or controlling processes on the cartridge and/or the sample. In particular, a test starts or begins with actuators acting on the cartridge. For example, a test can start with conveying the sample within the cartridge.

Methods and/or steps performed before insertion or receiving of the cartridge into/by the analysis device and/or before conveying, treating and/or preparing the sample within said cartridge are preferably not part of an assay, test or test procedure according to the present invention.

The above-mentioned aspects and features of the present invention and the aspects and features of the present invention that will become apparent from the claims and the following description can in principle be implemented independently from one another, but also in any combination or order.

Other aspects, advantages, features and properties of the present invention will become apparent from the claims and the following description of a preferred embodiment with reference to the accompanying drawings.

DETAILED DESCRIPTION OF THE INVENTION

In the following description, which are only schematic and sometimes not to scale, the same reference signs are used for the same or similar parts and components, corresponding or comparable properties, features and advantages, even if these are not repeatedly described.

Figure 1:
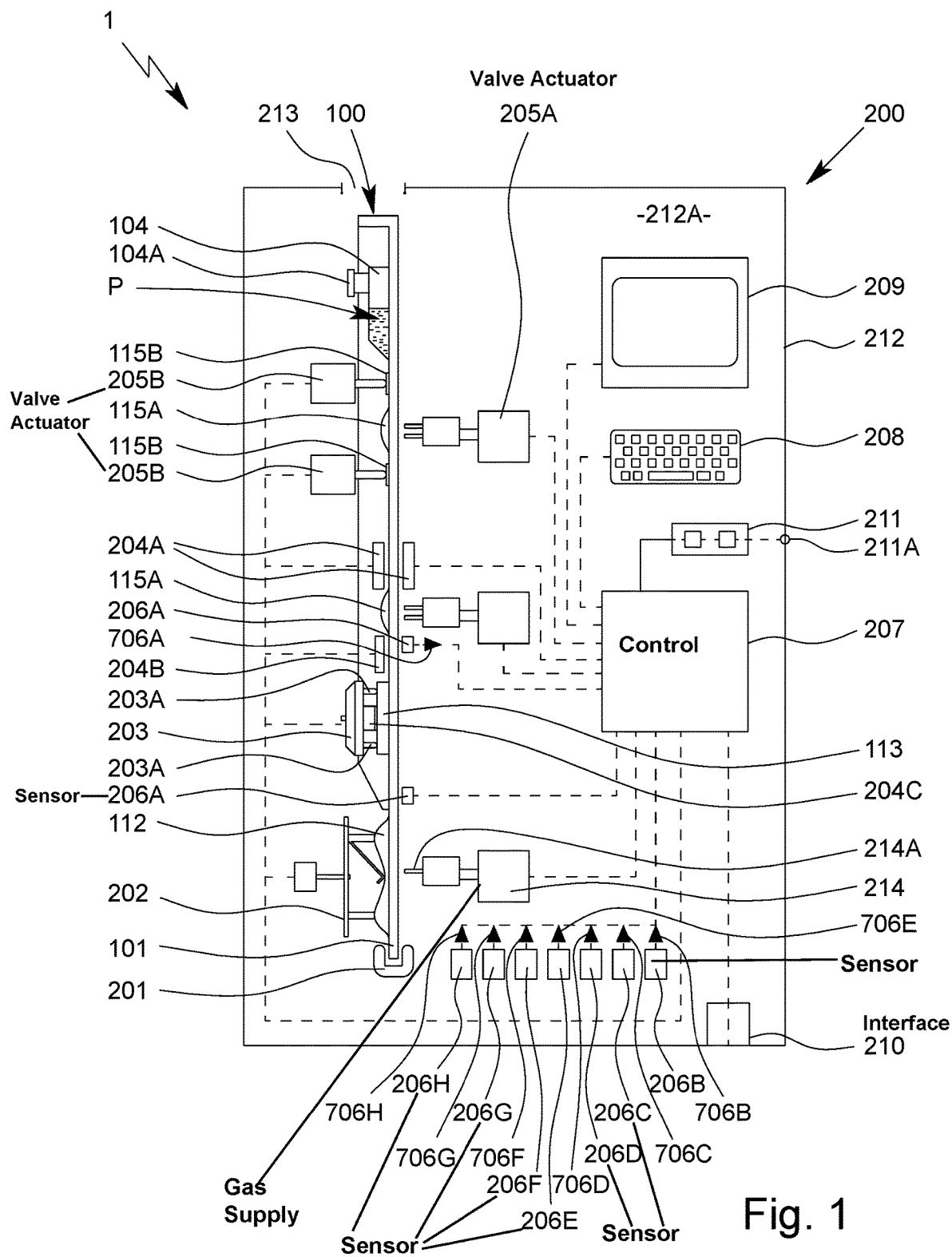
FIG. 1 is a schematic view of a proposed analysis device including a proposed cartridge received therein.

FIG. 1 is a highly schematic view of a proposed analysis system 1 and analysis device 200 for testing an in particular biological sample P, preferably by means of or in an apparatus or cartridge 100.

Figure 2:
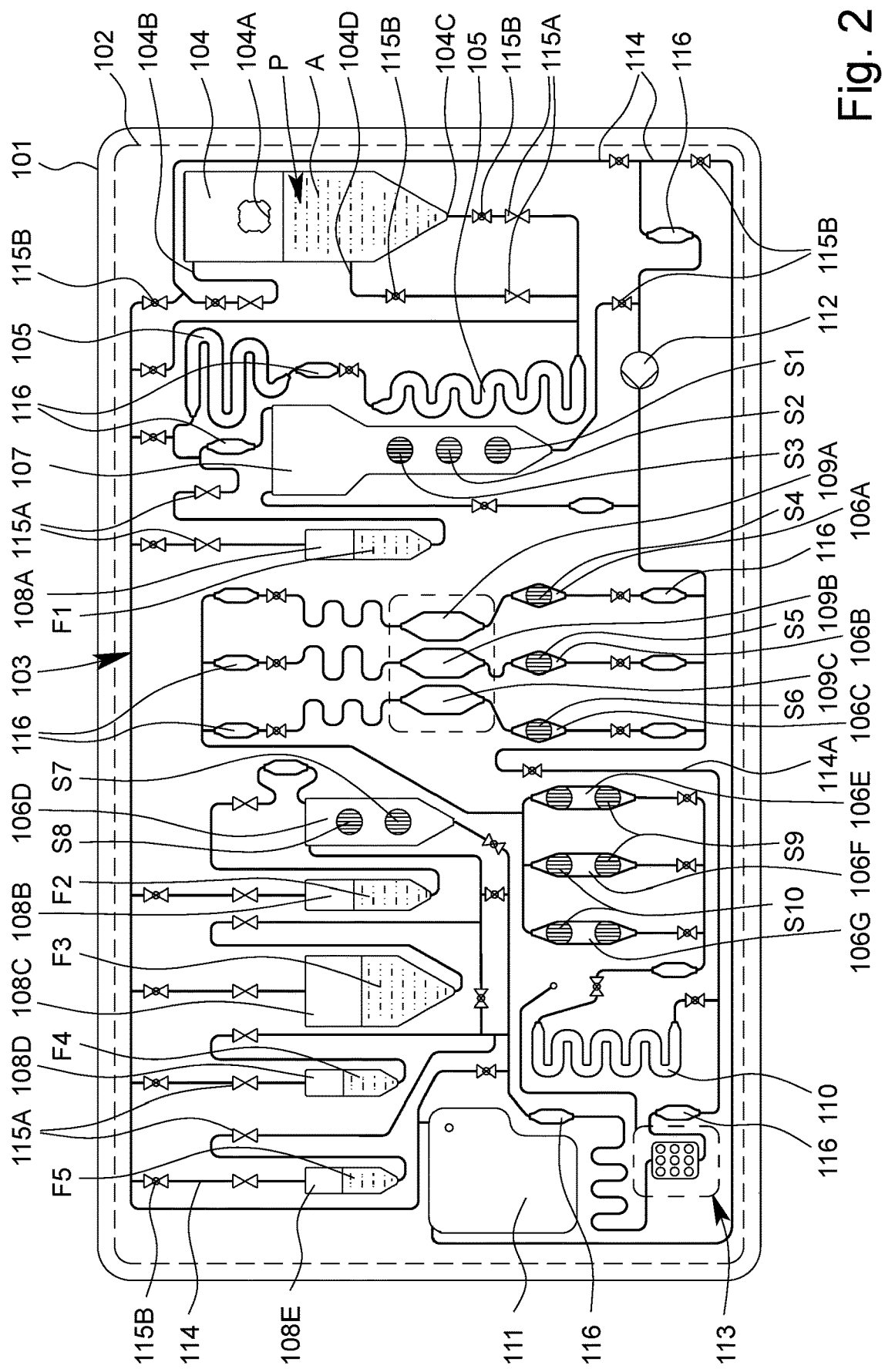
FIG. 2 is a schematic view of the cartridge.

FIG. 2 is a schematic view of a preferred embodiment of the proposed apparatus or cartridge 100 for testing the sample P. The apparatus or cartridge 100 in particular forms a handheld unit, and in the following is merely referred to as a cartridge.

The term "sample" is preferably understood to mean the sample material to be tested, which is in particular taken from a human or animal. In particular, within the meaning of the present invention, a sample is a fluid, such as saliva, blood, urine or another liquid, preferably from a human or animal, or a component thereof. Within the meaning of the present invention, a sample may be pretreated or prepared if necessary, or may come directly from a human or animal or the like, for example. A food sample, environmental sample or another sample may optionally also be tested, in particular for environmental analytics, food safety and/or for detecting other substances, preferably natural substances, but also biological or chemical warfare agents, poisons or the like.

Preferably, the analysis system 1 and/or analysis device 200 controls the testing of the sample P in particular in or on the cartridge 100 and/or is used to evaluate the testing and/or to collect, to process and/or to store measured values from the test.

The analysis system 1 preferably includes one or more cartridges 100 for receiving the sample P. The analysis system 1 preferably includes the analysis device 200 for receiving the cartridge 100 and subsequently carrying out the test using the received cartridge 100.

By means of the proposed analysis system 1, analysis device 200 and/or the cartridge 100 and/or using the proposed method for testing the sample P, preferably an analyte A of the sample P, in particular a (certain) nucleic-acid sequence and/or a (certain) protein, or particularly preferably a plurality of analytes A of the sample P, can be determined, identified or detected. Said analytes A are in particular detected, identified and/or measured not only qualitatively, but particularly preferably also quantitatively.

Therefore, the sample P can in particular be tested for qualitatively or quantitatively determining at least one analyte A, for example in order for it to be possible to detect a disease and/or pathogen or to determine other values, which are important for diagnostics, for example.

Particularly preferably, a molecular-biological test is made possible by means of the analysis system 1 and/or analysis device 200 and/or by means of the cartridge 100.

Particularly preferably, a nucleic-acid assay for detecting a nucleic-acid sequence, in particular a DNA sequence and/or RNA sequence, and/or a protein assay for detecting a protein, in particular an antigen and/or antibody, are made possible or are carried out.

Preferably, the sample P or individual components of the sample P or analyte A can be amplified if necessary, in particular by means of PCR, and tested, identified or detected in the analysis system 1, analysis device 200 and/or in the cartridge 100, and/or for the purpose of carrying out the nucleic-acid assay. Preferably, amplification products of the analyte A or analytes A are thus produced.

In the following, further details are first given on a preferred construction of the cartridge 100, with features of the cartridge 100 preferably also directly representing features of the analysis system 1, in particular even without any further explicit explanation.

The cartridge 100 is preferably at least substantially planar, flat, plate-shaped and/or card-like.

The cartridge 100 preferably includes an in particular at least substantially planar, flat, plate-shaped and/or card-like main body or support 101, the main body or support 101 in particular being made of and/or injection-molded from plastics material, particularly preferably polypropylene.

The cartridge 100 preferably includes at least one film or cover 102 for covering the main body 101 and/or cavities and/or channels formed therein at least in part, in particular on the front, and/or for forming valves or the like, as shown by dashed lines in FIG. 2.

The analysis system 1 or cartridge 100 or the main body 101 thereof, in particular together with the cover 102, preferably forms and/or includes a fluidic system 103, referred to in the following as the fluid system 103.

The cartridge 100, the main body 101 and/or the fluid system 103 are preferably at least substantially vertically oriented in the operating position and/or during the test, in particular in the analysis device 200, as shown schematically in FIG. 1. In particular, the main plane or surface extension of the cartridge 100 thus extends at least substantially vertically in the operating position.

The cartridge 100 and/or the fluid system 103 preferably includes a plurality of cavities, in particular at least one receiving cavity 104, at least one metering cavity 105, at least one intermediate cavity 106A-G, at least one mixing cavity 107, at least one storage cavity 108, at least one reaction cavity 109A-C, at least one intermediate temperature-control cavity 110 and/or at least one collection cavity 111, as shown in FIG. 1 and FIG. 2.

The cartridge 100 and/or the fluid system 103 also preferably includes at least one pump apparatus 112 and/or at least one sensor arrangement or sensor apparatus 113.

In general, the analysis device 200, the cartridge 100 or in particular the sensor apparatus 113 may measure, detect or identify the one or more analytes A by means of specific bonding, in particular by means of capture molecules and/or of means of electrochemical detection such as redox cycling, or the like, preferably performed on the cartridge 100 and/or in the sensor apparatus 113. Preferably, the capture molecules are arranged or immobilized on a sensor array or on sensor fields or electrodes of the sensor apparatus 113. In particular, an immuno-assay or a protein assay for detecting or identifying a protein and/or a nucleic-assay for detecting or identifying a nucleic-acid sequence can be or is realized.

Alternatively or additionally, measurements without specific bonding and/or without electrochemical detection can be used or performed, preferably in or by the analysis device 200 and/or cartridge 100. Such measurements can include an optical measurement, impedance measurement, capacitance measurement, spectrometric measurement, mass spectrometric measurement, or the like. For this purpose, the analysis device 200 or cartridge 100 may include an optical spectrometer and/or allow optical measurements of the treated or untreated sample P. Thus, it is possible to measure, detect or identify other or further analytes A, compounds, material characteristics, or the like of the sample P, e.g. within the cartridge 100 or any other sample carrier. These alternative or additional measurements can be used or processed and/or evaluated in a similar manner as described or differently.

Some, most or all of the cavities are preferably formed by chambers and/or channels or other depressions in the cartridge 100 and/or the main body 101, and particularly preferably are covered or closed by the cover 102. However, other structural solutions are also possible.

In the example shown, the cartridge 100 or the fluid system 103 preferably includes two metering cavities 105, a plurality of intermediate cavities 106A to 106G, a plurality of storage cavities 108A to 108E and/or a plurality of reaction cavities 109A-C, which can preferably be loaded separately from one another, in particular a first reaction cavity 109A, a second reaction cavity 109B and an optional third reaction cavity 109C, as can be seen in FIG. 2.

The reaction cavity/cavities 109A-C is/are used in particular to carry out an amplification reaction, in particular PCR, or several, preferably different, amplification reactions, in particular PCRs. It is preferable to carry out several, preferably different, PCRs, i.e. PCRs having different primer combinations or primer pairs, in parallel and/or independently and/or in different reaction cavities 109A-C.

To carry out the nucleic-acid assay, preferably nucleic-acid sequences, as analytes A of the sample P, are amplified in the reaction cavity/cavities 109A-C by means of an amplification reaction, in particular in order to produce amplification products for the subsequent detection in the sensor arrangement or sensor apparatus 113.

Within the meaning of the present invention, amplification reactions are in particular molecular-biological reactions in which an analyte A, in particular a nucleic-acid sequence, is amplified/copied and/or in which amplification products, in particular nucleic-acid products, of an analyte A are produced. Particularly preferably, PCRs are amplification reactions within the meaning of the present invention.

The amplification products V and/or other portions of the sample P produced in the one or more reaction cavities 109A-C can be conducted or fed to the connected sensor arrangement or sensor apparatus 113, in particular by means of the pump apparatus 112.

The sensor apparatus 113 is used in particular for detecting, particularly preferably qualitatively and/or quantitatively determining, the analyte A or analytes A of the sample P, in this case particularly preferably the nucleic-acid sequences and/or proteins as the analytes A. Alternatively or additionally, however, other values may also be collected or determined.

As already explained at the outset, in particular nucleic-acid sequences, preferably DNA sequences and/or RNA sequences, and/or proteins, in particular antigens and/or antibodies, are preferably qualitatively and/or quantitatively determined as analytes A of the sample P. In the following, however, a distinction is not made between nucleic-acid sequences and proteins, or between the nucleic-acid assay for detecting nucleic-acid sequences and the protein assay for detecting proteins.

In particular, the pump apparatus 112 includes or forms a tube-like or bead-like raised portion, in particular by means of the film or cover 102, particularly preferably on the back of the cartridge 100, as shown schematically in FIG. 1. However, the pump apparatus 112 can be realized differently as well.

The cartridge 100, the main body 101 and/or the fluid system 103 preferably include a plurality of channels 114 and/or valves 115A, 115B, as shown in FIG. 2.

By means of the channels 114 and/or valves 115A, 115B, the cavities 104 to 111, the pump apparatus 112 and/or the sensor arrangement and/or sensor apparatus 113 can be temporarily and/or permanently fluidically interconnected and/or fluidically separated from one another, as required and/or optionally or selectively, in particular such that they are controlled by the analysis system 1 or the analysis device 200.

The cavities 104 to 111 are preferably each fluidically linked or interconnected by a plurality of channels 114. Particularly preferably, each cavity is linked or connected by at least two associated channels 114, in order to make it possible for fluid to fill, flow through and/or drain from the respective cavities as required.

The fluid transport or the fluid system 103 is preferably not based on capillary forces, or is not exclusively based on said forces, but in particular is essentially based on the effects of gravity and/or pumping forces and/or compressive forces and/or suction forces that arise, which are particularly preferably generated by the pump or pump apparatus 112. In this case, the flows of fluid or the fluid transport and the metering are controlled by accordingly opening and closing the valves 115A, 115B and/or by accordingly operating the pump or pump apparatus 112, in particular by means of a pump drive 202 of the analysis device 200.

Preferably, each of the cavities 104 to 110 has an inlet at the top and an outlet at the bottom in the operating position. Therefore, if required, only liquid from the respective cavities can be removed via the outlet.

In the operating position, the liquids from the respective cavities are preferably removed, in particular drawn out, via the outlet that is at the bottom in each case, it preferably being possible for gas or air to flow and/or be pumped into the respective cavities via the inlet that is in particular at the top. In particular, relevant vacuums in the cavities can thus be prevented or at least minimized when conveying the liquids.

In particular, the cavities, particularly preferably the storage cavity/cavities 108, the mixing cavity 107 and/or the receiving cavity 104, are each dimensioned and/or oriented in the normal operating position such that, when said cavities are filled with liquid, bubbles of gas or air that may potentially form rise upwards in the operating position, such that the liquid collects above the outlet without bubbles. However, other solutions are also possible here.

The receiving cavity 104 preferably includes a connection 104A for introducing the sample P. In particular, the sample P may for example be introduced into the receiving cavity 104 and/or cartridge 100 via the connection 104A by means of a pipette, syringe or other instrument.

The receiving cavity 104 preferably includes an inlet 104B, an outlet 104C and an optional intermediate connection 104D, it preferably being possible for the sample P or a portion thereof to be removed and/or conveyed further via the outlet 104C and/or the optional intermediate connection 104D. Gas, air or another fluid can flow in and/or be pumped in via the inlet 104B, as already explained.

Preferably, the sample P or a portion thereof can be removed, optionally and/or depending on the assay to be carried out, via the outlet 104C or the optional intermediate connection 104D of the receiving cavity 104. In particular, a supernatant of the sample P, such as blood plasma or blood serum, can be conducted away or removed via the optional intermediate connection 104D, in particular for carrying out the protein assay.

Preferably, at least one valve 115A, 115B is assigned to each cavity, the pump apparatus 112 and/or the sensor apparatus 113 and/or is arranged upstream of the respective inlets and/or downstream of the respective outlets.

Preferably, the cavities 104 to 111 or sequences of cavities 104 to 111, through which fluid flows in series or in succession for example, can be selectively released and/or fluid can selectively flow therethrough by the assigned valves 115A, 115B being actuated, and/or said cavities can be fluidically connected to the fluid system 103 and/or to other cavities.

In particular, the valves 115A, 115B are formed by the main body 101 and the film or cover 102 and/or are formed in another manner, for example by additional layers, depressions or the like.

Particularly preferably, one or more valves 115A are provided which are preferably tightly closed initially or in the storage state, particularly preferably in order to seal liquids or liquid reagents F, located in the storage cavities 108, and/or the fluid system 103 from the open receiving cavity 104 in a storage-stable manner.

Preferably, an initially closed valve 115A is arranged upstream and downstream of each storage cavity 108. Said valves are preferably only opened, in particular automatically, when the cartridge 100 is actually being used and/or while inserting the cartridge 100 into the analysis device 200 and/or for carrying out the assay.

A plurality of valves 115A, in particular three valves in this case, are preferably assigned to the receiving cavity 104, in particular if the intermediate connection 104D is provided in addition to the inlet 104B and the outlet 104C. Depending on the use, in addition to the valve 115A on the inlet 104B, then preferably only the valve 115A either at the outlet 104C or at the intermediate connection 104D is opened.

The valves 115A assigned to the receiving cavity 104 seal the fluid system 103 and/or the cartridge 100 in particular fluidically and/or in a gas-tight manner until the sample P is inserted and the receiving cavity 104 or a connection 104A of the receiving cavity 104 is closed.

As an alternative or in addition to the valves 115A (which are initially closed), one or more valves 115B are preferably provided which are not closed in a storage-stable manner and/or which are open initially and/or which can be closed by actuation. These valves are used in particular to control the flows of fluid during the test.

The cartridge 100 is preferably designed as a microfluidic card and/or the fluid system 103 is preferably designed as a microfluidic system. In the present invention, the term "microfluidic" is preferably understood to mean that the respective volumes of individual cavities, some of the cavities or all of the cavities 104 to 111 and/or channels 114 are, separately or cumulatively, less than 5 ml or 2 ml, particularly preferably less than 1 ml or 800 µl, in particular less than 600 µl or 300 µl, more particularly preferably less than 200 µl or 100 µl.

Particularly preferably, a sample P having a maximum volume of 5 ml, 2 ml or 1 ml can be introduced into the cartridge 100 and/or the fluid system 103, in particular the receiving cavity 104.

Reagents and liquids which are preferably introduced or provided before the test in liquid form as liquids or liquid reagents F and/or in dry form as dry reagents S are required for testing the sample P, as shown in the schematic view according to FIG. 2 by reference signs F1 to F5 and S1 to S10.

Furthermore, other liquids F, in particular in the form of a wash buffer, solvent for dry reagents S and/or a substrate, for example in order to form detection molecules and/or a redox system, are also preferably required for the test, the detection process and/or for other purposes, and are in particular provided in the cartridge 100, i.e. are likewise introduced before use, in particular before delivery. At some points in the following, a distinction is not made between liquid reagents and other liquids, and therefore the respective explanations are accordingly also mutually applicable.

The analysis system 1 or the cartridge 100 preferably contains all the reagents and liquids required for pretreating the sample P and/or for carrying out the test or assay, in particular for carrying out one or more amplification reactions or PCRs, and therefore, particularly preferably, it is only necessary to receive the optionally pretreated sample P.

The cartridge 100 or the fluid system 103 preferably includes a bypass 114A that can optionally be used, in order for it to be possible, if necessary, to conduct or convey the sample P or components thereof past the reaction cavities 109A-C and/or, by bypassing the optional intermediate temperature-control cavity 110, also directly to the sensor apparatus 113.

The cartridge 100, the fluid system 103 and/or the channels 114 preferably include sensor portions 116 or other apparatuses for detecting liquid fronts and/or flows of fluid, in particular of the sample P into, through and/or out of the sensor portion 116.

It is noted that various components, such as the channels 114, the valves 115A, 115B, in particular the valves 115A that are initially closed and the valves 115B that are initially open, and the sensor portions 116 in FIG. 2 are, for reasons of clarity, only labelled in some cases, but the same symbols are used in FIG. 2 for each of these components.

The collection cavity 111 is preferably used for receiving excess or used reagents and liquids and volumes of the sample, and/or for providing gas or air in order to empty individual cavities and/or channels.

In particular, the collection cavity 111 can optionally be connected to individual cavities and channels or other apparatuses fluidically in order to remove reagents and liquids from said cavities, channels or other apparatuses and/or to replace said reagents and liquids with gas or air. The collection cavity 111 is preferably given appropriate large dimensions.

Once the sample P has been introduced into the receiving cavity 104 and the connection 104A has been closed, the cartridge 100 can be inserted into and/or received in the proposed analysis device 200 in order to test the sample P, as shown in FIG. 1. Alternatively, the sample P could also be fed in later.

FIG. 1 shows the analysis system 1 in a ready-to-use state for carrying out a test or assay on the sample P received in the cartridge 100. In this state, the cartridge 100 is therefore linked to, received by and/or inserted into the analysis device 200.

In the following, some features and aspects of the analysis device 200 are first explained in greater detail, in particular on the basis of FIG. 1. The features and aspects relating to said device are preferably also directly features and aspects of the proposed analysis system 1, in particular even without any further explicit explanation.

The analysis system 1 or analysis device 200 preferably includes a mount or receptacle 201 for mounting and/or receiving the cartridge 100.

Preferably, the cartridge 100 is fluidically, in particular hydraulically, separated or isolated from the analysis device 200. In particular, the cartridge 100 forms a preferably independent and in particular closed or sealed fluidic or hydraulic system 103 for the sample P and the reagents and other liquids. In this way, the analysis device 200 does not come into direct contact with the sample P and can in particular be reused for another test without being disinfected and/or cleaned first.

It is however provided that the analysis device 200 can be connected or coupled mechanically, electrically, thermally and/or pneumatically to the cartridge 100.

In particular, the analysis device 200 is designed to have a mechanical effect, in particular for actuating the pump apparatus 112 and/or the valves 115A, 115B, and/or to have a thermal effect, in particular for temperature-controlling the reaction cavity/cavities 109A-C and/or the intermediate temperature-control cavity 110.

In addition, the analysis device 200 can preferably be pneumatically connected to the cartridge 100, in particular in order to actuate individual apparatuses, and/or can be electrically connected to the cartridge 100, in particular in order to collect and/or transmit measured values, for example from the sensor apparatus 113 and/or sensor portions 116.

The analysis system 1 or analysis device 200 preferably includes a pump drive 202, the pump drive 202 in particular being designed for mechanically actuating the pump apparatus 112.

Preferably, a head of the pump drive 202 can be rotated in order to rotationally axially depress the preferably bead-like raised portion of the pump apparatus 112. Particularly preferably, the pump drive 202 and pump apparatus 112 together form a pump, in particular in the manner of a hose pump or peristaltic pump and/or a metering pump, for the fluid system 103 and/or the cartridge 100.

Particularly preferably, the pump is constructed as described in DE 10 2011 015 184 B4. However, other structural solutions are also possible.

Preferably, the capacity and/or discharge rate of the pump can be controlled and/or the conveying direction of the pump and/or pump drive 202 can be switched. Preferably, fluid can thus be pumped forwards or backwards as desired.

The analysis system 1 or analysis device 200 preferably includes a connection apparatus 203 for in particular electrically and/or thermally connecting the cartridge 100 and/or the sensor arrangement or sensor apparatus 113.

As shown in FIG. 1, the connection apparatus 203 preferably includes a plurality of electrical contact elements 203A, the cartridge 100, in particular the sensor arrangement or sensor apparatus 113, preferably being electrically connected or connectable to the analysis device 200 by the contact elements 203A.

The analysis system 1 or analysis device 200 preferably includes one or more temperature-control apparatuses for temperature-controlling the cartridge 100 and/or having a thermal effect on the cartridge 100, in particular for heating and/or cooling, the temperature-control apparatus(es) (each) preferably including or being formed by a heating resistor or a Peltier element.

Individual temperature-control apparatuses, some of these apparatuses or all of these apparatuses can preferably be positioned against or abutted on the cartridge 100, the main body 101, the cover 102, the sensor arrangement, sensor apparatus 113 and/or individual cavities and/or can be thermally coupled thereto and/or can be integrated therein and/or in particular can be operated or controlled electrically by the analysis device 200. In the example shown, in particular the temperature-control apparatuses 204A-C are provided.

Preferably, the temperature-control apparatus 204A, referred to in the following as the reaction temperature-control apparatus 204A, is assigned to one of the reaction cavities 109A-C or to a plurality of reaction cavities 109A-C, in particular in order for it to be possible to carry out one or more amplification reactions therein.

The reaction cavities 109A-C are preferably temperature-controlled simultaneously and/or uniformly, in particular by means of one common reaction temperature-control apparatus 204A or two reaction temperature-control apparatuses 204A.

More particularly preferably, the reaction cavity/cavities 109A-C can be temperature-controlled from two different sides and/or by means of two or the reaction temperature-control apparatuses 204A that are preferably arranged on opposite sides.

Alternatively, each reaction cavity 109A-C can be temperature-controlled independently and/or individually.

The temperature-control apparatus 204B, referred to in the following as the intermediate temperature-control apparatus 204B, is preferably assigned to the intermediate temperature-control cavity 110 and/or is designed to (actively) temperature-control or heat the intermediate temperature-control cavity 110 and/or a fluid located therein, in particular the amplification products, preferably to a preheat temperature.

The intermediate temperature-control cavity 110 and/or intermediate temperature-control apparatus 204B is preferably arranged upstream of or (immediately) before the sensor arrangement or sensor apparatus 113, in particular in order for it to be possible to temperature-control or preheat, in a desired manner, fluids to be fed to the sensor arrangement or sensor apparatus 113, in particular analytes A and/or amplification products, particularly preferably immediately before said fluids are fed.

Particularly preferably, the intermediate temperature-control cavity 110 or intermediate temperature-control apparatus 204B is designed or provided to denature the sample P or analytes A and/or the amplification products V produced, and/or to divide any double-stranded analytes A or amplification products into single strands and/or to counteract premature bonding or hybridizing of the amplification products V, in particular by the addition of heat.

Preferably, the analysis system 1, analysis device 200 and/or the cartridge 100 and/or one or each temperature-control apparatus include/includes a temperature detector and/or temperature sensor (not shown), in particular in order to make it possible to control and/or feedback control temperature.

One or more temperature sensors may for example be assigned to the sensor portions 116 and/or to individual channel portions or cavities, i.e. may be thermally coupled thereto.

The temperature-control apparatus 204C, referred to in the following as the sensor temperature-control apparatus 204C, is in particular assigned to the sensor apparatus 113 and/or is designed to (actively) temperature-control or heat fluids located in or on the sensor arrangement or sensor apparatus 113, in particular analytes A and/or amplification products, reagents or the like, in a desired manner, preferably to a hybridization temperature.

The sensor temperature-control apparatus 204C is preferably planar and/or has a contact surface which is preferably rectangular and/or corresponds to the dimensions of the sensor arrangement or sensor apparatus 113, the contact surface allowing for heat transfer between the sensor temperature-control apparatus 204C and the sensor apparatus 113.

Preferably, the analysis device 200 includes the sensor temperature-control apparatus 204C. However, other structural solutions are also possible in which the sensor temperature-control apparatus 204C is integrated in the cartridge 100, in particular the sensor arrangement or sensor apparatus 113.

Particularly preferably, the connection apparatus 203 includes the sensor temperature-control apparatus 204C, and/or the connection apparatus 203 together with the sensor temperature-control apparatus 204C can be linked to, in particular pressed against, the cartridge 100, in particular the sensor arrangement or sensor apparatus 113.

More particularly preferably, the connection apparatus 203 and the sensor temperature-control apparatus 204C (together) can be moved towards and/or relative to the cartridge 100, in particular the sensor arrangement or sensor apparatus 113, and/or can be positioned against said cartridge, preferably in order to both electrically and thermally couple the analysis device 200 to the cartridge 100, in particular the sensor arrangement or sensor apparatus 113 or the support thereof.

Preferably, the sensor temperature-control apparatus 204C is arranged centrally on the connection apparatus 203 or a support thereof and/or is arranged between the contact elements 203A.

In particular, the contact elements 203A are arranged in an edge region of the connection apparatus 203 or a support thereof or are arranged around the sensor temperature-control apparatus 204C, preferably such that the connection apparatus 203 is connected or connectable to the sensor apparatus 113 thermally in the center and electrically on the outside or in the edge region. However, other solutions are also possible here.

The analysis system 1 or analysis device 200 preferably includes one or more valve actuators 205A, B for actuating the valves 115A, 115B. Particularly preferably, different (types or groups of) valve actuators 205A and 205B are provided which are assigned to the different (types or groups of) valves 115A and 115B for actuating each of said valves, respectively.

The analysis system 1 or analysis device 200 preferably includes a control apparatus 207 for controlling the sequence of a test or assay and/or for collecting, evaluating and/or outputting or providing measured values in particular from the sensor apparatus 113, and/or test results and/or other data or values.

The control apparatus 207 preferably includes an internal clock or time base by means of which the sequence of the test is or can be controlled and/or by means of which test steps that follows temporally one another or that extend over time are controlled or can be controlled by the control apparatus 207.

The control apparatus 207 preferably controls or is designed to control actuators of the analysis device 200 for acting on the cartridge 100 in order to carry out the test. The actuators are in particular the pump drive 202, the temperature-control apparatuses and/or the valve actuators 205A, B.

The analysis system 1 or analysis device 200 preferably includes one or more sensors 206A-H.

In one aspect of the present invention, which can also be implemented independently, one or more fluid sensors 206A are designed, provided or intended to detect liquid fronts PF1, PF2 and/or flows of fluid in the fluid system 103.

Particularly preferably, the fluid sensors 206A are designed to measure or detect, for example optically and/or capacitively, a liquid front PF1, PF2 and/or the presence, the speed, the mass flow rate/volume flow rate, the temperature and/or another value of a fluid in a channel and/or a cavity, in particular in a respectively assigned sensor portion 116, which is in particular formed by a planar and/or widened channel portion of the fluid system 103.

The fluid sensor/fluid sensors 206A preferably measures/measure a fluid or a liquid entering or leaving the sensor portion 116 and/or a content change or fluid change in the sensor portion 116, and in the process generates a measurement result 706A that corresponds to the fluid entering, the fluid leaving, the content change and/or the fluid change in the sensor portion 116.

This measurement result 706A from the fluid sensor 206A can be retrieved by the control apparatus 207 and/or transmitted to the control apparatus 207. The control apparatus 207 controls or is designed to control the test and/or the actuators, preferably using or taking into account the measurement result 706A from the fluid sensor 206A. However, different approaches to control the test based on the measurement result 206A are possible.

In particular, when a content change, an entering fluid, a leaving fluid and/or a fluid change is detected in the sensor portion 116, in particular when a liquid front PF1, PF2 is detected, the control apparatus 207 influences a program sequence. In this case, for example a control can be carried out or a subsequent step of the test can be controlled, in particular by activating the actuators in a particular and/or differing manner.

Particularly preferably, the sensor portions 116 are each oriented and/or incorporated in the fluid system 103 and/or fluid flows against or through the sensor portions 116 such that, in the operating position of the cartridge 100, fluid flows through the sensor portions 116 in the vertical direction and/or from the bottom to the top, or vice versa, in particular in order to make it possible or easier to accurately detect liquid.

Alternatively, or additionally, the analysis device 200 preferably includes one or more (different, other and/or further) sensors 206B-206H which preferably generate or are designed to generate measurement results 706 B-H.

The sensor 206B can be a pressure sensor for determining the (relative) air pressure.

Alternatively, or additionally, one or more temperature sensors 206C are provided for detecting the internal temperature and/or the temperature in the interior space 212A of the analysis device 200, in particular the temperature of an atmosphere in the interior space 212A.

Alternatively, or additionally, one or more temperature sensors 206C are provided for detecting the ambient temperature and/or the temperature of an atmosphere surrounding the analysis device 200 and/or the temperature of one or more of the temperature-control apparatuses.

The analysis device 200 preferably includes a tilt sensor 206D for detecting the inclination and/or orientation of the analysis device 200 and/or of the cartridge 100.

The analysis device 200 may include an acceleration sensor 206E. The acceleration sensor 206E is preferably designed to determine an acceleration of the analysis device 200, in particular an acceleration in the vertical and/or horizontal direction with respect to the operating position.

The analysis device 200 may include a humidity sensor 206F for determining the (relative) atmospheric humidity and/or the dew point of the atmosphere inside or in the interior space 212A and/or outside the analysis device 200.

The analysis device 200 may include a position sensor 206G for determining the position or location, for example by means of a GPS sensor. The position sensor 206G is preferably designed to determine the location of the analysis device in space, in particular on the Earth's surface, and/or to output the geographical position, the location and/or the coordinates of the analysis device 200.

The analysis device 200 may include a cartridge sensor 206H for determining or checking the position or alignment of the cartridge 100 in or with respect to the analysis device 200.

The control apparatus 207 preferably controls or is designed to control the test and/or the actuators, preferably using or taking into account one or more of the measurement results 706A-H from the sensors 206A-H. In this case, the control apparatus 207 preferably controls or feedback controls actuators such that they act on the cartridge 100 in order to carry out the test. In particular, the control apparatus 207 controls the pump drive 202, the temperature-control apparatuses 204 and/or valve actuators 205, in particular taking into account or depending on one or more of the measured values 706A-H from one or more of the sensors 206A-H.

The flows of fluid are controlled in particular by accordingly activating the pump or pump apparatus 112 and actuating the valves 115A, 115B. Particularly preferably, the pump drive 202 includes a stepper motor, or a drive calibrated in another way, such that desired metering can be achieved, at least in principle, by means of appropriate activation.

Additionally or alternatively, the fluid sensors 206A are used to detect liquid fronts PF1, PF2 or flows of fluid, in particular in cooperation with the assigned sensor portions 116, in order to achieve the desired fluidic sequence and the desired metering by accordingly controlling the pump or pump apparatus 112 and accordingly activating the valves 115A, 115B.

Optionally, the analysis system 1 or analysis device 200 includes an input apparatus 208, such as a keyboard, a touch screen or the like, and/or a display apparatus 209, such as a screen.

The analysis system 1 or analysis device 200 preferably includes at least one interface 210, for example, for controlling, for communicating and/or for outputting measured data or test results and/or for linking to other devices, such as a printer, an external power supply or the like. This may in particular be a wired or wireless interface 210.

The analysis system 1 or analysis device 200 preferably includes a power supply 211, preferably a battery or an accumulator, which is in particular integrated and/or externally connected or connectable. Preferably, an integrated accumulator is provided as a power supply 211 and can be (re)charged by an external charging device (not shown) via a connection 211A and/or is interchangeable.

The analysis system 1 or analysis device 200 preferably includes a housing 212, all the components and/or some or all of the apparatuses preferably being integrated in the housing 212. Particularly preferably, the cartridge 100 can be inserted or slid into the housing 212, and/or can be received by the analysis device 200, through an opening 213 which can in particular be closed, such as a slot or the like.

The analysis system 1 or analysis device 200 is preferably portable or mobile. Particularly preferably, the analysis device 200 weighs less than 25 kg or 20 kg, particularly preferably less than 15 kg or 10 kg, in particular less than 9 kg or 6 kg.

The fluidic, in particular pneumatic, coupling between the cartridge 100 and the analysis device 200 will be explained in greater detail in the following, it being possible for the following aspects to be implemented independently from the preceding aspects.

As already explained, the analysis device 200 can preferably be pneumatically linked to the cartridge 100, in particular to the sensor arrangement or sensor apparatus 113 and/or to the pump apparatus 112.

Particularly preferably, the analysis device 200 is designed to supply the cartridge 100, in particular the sensor arrangement or sensor apparatus 113 and/or the pump apparatus 112, with a working medium, in particular gas or air.

Preferably, the working medium can be compressed and/or or pressurized in the analysis device 200 or by means of the analysis device 200.

Preferably, the analysis device 200 includes a pressurized gas supply 214 for this purpose, in particular a pressure generator or compressor, preferably in order to compress and/or pressurize the working medium.

The pressurized gas supply 214 is preferably integrated in the analysis device 200 or the housing 212 and/or can be controlled or feedback controlled by means of the control apparatus 207. The pressurized gas supply 214 can also, at least in part, be formed on or by the cartridge 100.

Preferably, the pressurized gas supply 214 is electrically operated or can be operated by electrical power. In particular, the pressurized gas supply 214 can be supplied with electrical power by means of the power supply 211.

The analysis device 200 or pressurized gas supply 214 is preferably designed to compress the working medium to a pressure of more than 100 kPa, particularly preferably more than 150 kPa or 250 kPa, in particular more than 300 kPa or 350 kPa, and/or of less than 1 MPa, particularly preferably less than 900 kPa or 800 kPa, in particular less than 700 kPa and/or to feed said medium to the cartridge 100 at said pressure.

Preferably, air can be drawn in, in particular from the surroundings, as the working medium by means of the analysis device 200 or pressurized gas supply 214. In particular, the analysis device 200 or pressurized gas supply 214 is designed to use the surroundings as a reservoir for the working medium or the air. However, other solutions are also possible here, in particular those in which the analysis device 200 or pressurized gas supply 214 includes a preferably closed or delimited reservoir, such as a tank or container, including the working medium, and/or is connected or connectable thereto.

Preferably, the analysis device 200 or pressurized gas supply 214 includes an inlet, the working medium in particular being able to be drawn in and/or conducted in the pressurized gas supply 214 via the inlet.

Preferably, the analysis device 200 or pressurized gas supply 214 includes a filter, the filter preferably being integrated in the inlet and/or it preferably being possible for the working medium to be filtered by means of the filter and/or it preferably being possible for particles to be separated from the working medium by means of the filter.

The filter is preferably designed as a micro filter or as a fine particulate air filter. Preferably, particles having a particle diameter of more than 10 μm, particularly preferably more than 8 μm or 9 μm, in particular more than 6 μm or 7 μm, more particularly preferably more than 4 μm or 5 μm, can be separated by means of the filter, the particle diameter preferably being the maximum or average diameter of the respective particles. This ensures that the channels or lines in the cartridge that convey the working medium do not become contaminated or clogged and/or that no undesired pressure loss occurs.

The analysis device 200 or pressurized gas supply 214 preferably includes a connection element 214A, in particular in order to pneumatically connect the analysis device 200 and/or pressurized gas supply 214 to the cartridge 100.

Figure 3:
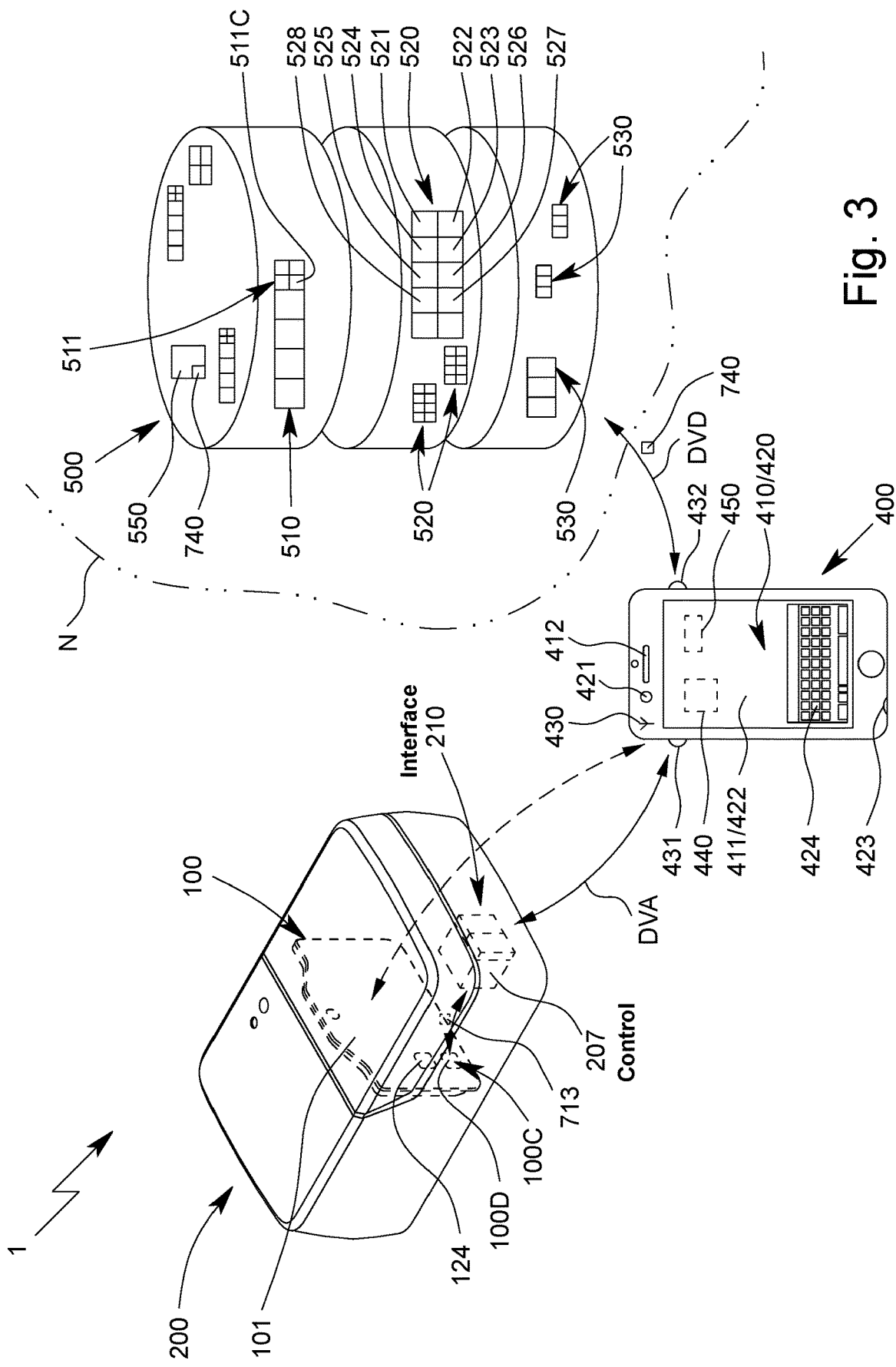
FIG. 3 is a schematic view of the proposed analysis system.

FIG. 3 is a schematic view of the proposed analysis system 1 for testing an in particular biological sample P, including the analysis device 200 for receiving the cartridge 100 and subsequently carrying out the test using the received cartridge 100, and an operating instrument 400 for the analysis device 200.

The operating instrument 400 is preferably designed to control the analysis device 200. Alternatively or additionally, the operating instrument 400 can receive or retrieve information, in particular (measurement) results such as measured values, from the analysis device 200. In particular, the operating instrument 400 is a mobile terminal device such as a smartphone, a tablet or the like.

The operating instrument 400 is preferably implemented or provided so as to be physically separated from the analysis device 200. The operating instrument 400 can preferably be separated and/or disconnected from the analysis device 200 physically and/or with respect to a data connection.

The operating instrument 400 can preferably be wirelessly connected to the analysis device 200. A data connection DVA can thus be established between the analysis device 200 and the operating instrument 400. However, the data connection DVA can in principle also be established in another manner, for example wired.

It is preferable for the operating instrument 400 to also be operational when separated or disconnected from the analysis device 200, in particular for carrying out evaluations or for other purposes. Alternatively, or additionally, the analysis device 200 is also operational when separated or disconnected from the operating instrument 400, in particular for continuing a test.

Particularly preferably, the operating instrument 400 includes an interface 430 for establishing data connections DVA, DVD. The interface 430 and/or the operating instrument 400 in particular includes what is referred to as an analysis device interface 431 that is designed to establish the preferably wireless data connection DVA to the analysis device 200. This can, for example, be a radio interface, WPAN interface, Bluetooth interface and/or a Bluetooth module or the like.

The interface 210 of the analysis device 200 preferably corresponds to the interface 430 and/or the analysis device interface 431 of the operating instrument 400, in particular such that the data connection DVA between the operating instrument 400 and the analysis device 200 can be established. The interface 210 of the analysis device 200 and the analysis device interface 431 preferably support the same data transmission method and/or radio transmission method or radio standard, in particular WLAN or WPAN methods such as Bluetooth, NFC, Zigbee or the like.

Particularly preferably, the interface 210 of the analysis device 200 and the analysis device interface 431 make possible or facilitate what is known as an ad-hoc connection. In this case, the data connection DVA is established preferably automatically when the devices, i.e. the operating instrument 400 and the analysis device 200, are within range of one another.

In order to control the test, it is preferable for precisely one data connection DVA to be provided between the analysis device 200 to be controlled and the operating instrument 400 controlling the analysis device 200, and/or for control information 510 to be received and/or accepted or to be acceptable and/or receivable and/or for measurement results 713 to be transmitted or to be transmittable only via precisely one data connection DVA between the analysis device 200 to be controlled and the operating instrument 400 controlling the analysis device 200.

The analysis system 1 preferably further includes a database 500 or the database 500 is assigned to the analysis system 1. The database 500 is preferably an external database 500 that is implemented or provided so as to be physically separated from the operating instrument 400 and/or from the analysis device 200. In principle, however, it is not impossible for the database 500 to be provided or implemented such that it can be directly linked, in particular to the operating instrument 400, or to be provided or implemented by the operating instrument 400.

The operating instrument 400 can access the database 500 via a data connection DVD. For this purpose, the operating instrument 400 and/or the interface 430 can include a database interface 432 by means of which the database 500 can be accessed, in particular via a network N. The network N may be the Internet or another data network N. It is also preferable for the operating instrument 400 to be able to establish the data connection DVD to the database 500 via a wireless interface, in particular WLAN, WPAN, mobile communications or the like. However, in principle, other solutions are also possible here.

The analysis system 1, in particular the database 500, preferably includes control information 510 by means of which the analysis device 200 can be controlled in order to carry out a test.

The control information 510 preferably defines the actuation of the actuators of the analysis device 200 in a particular manner, such that the sample P is tested in the cartridge 100.

In particular, actuators for carrying out the test can be or are controlled using the control information 510 such that said actuators act on the cartridge 100 and/or the sample P. These actuators are in particular the pump drive 202 and/or one or more temperature-control apparatuses 204 and/or one or more valve actuators 205. The control information 510 preferably includes parameters and/or instructions for carrying out one or more steps of the method for testing the sample P explained above.

Alternatively or additionally, the control information 510 includes execution information 511 for executing the test, in particular the sequence for controlling different actuators. The execution information 511 can also be separate from the control information 510, can be stored in the database 500 and/or can be transmitted to the analysis device 200 and/or the operating instrument 400.

Preferably, the analysis system 1 includes calibration information 520 that can be stored in the database 500 and/or can be retrieved from the database 500. The calibration information 520 is preferably capable of influencing the test of the sample P, in particular depending on the specific cartridge 100, on a cartridge batch of the specific cartridge 100 and/or on the specific test.

The calibration information 520 is in particular default or basic settings, parameters and/or threshold values for sensors such as the sensor apparatus 113 of the cartridge 100, for one or more of the sensor(s) 206A-H of the analysis device 200 and/or for one or more of the actuators.

Calibration information 520 can be used in addition to control information 510 for carrying out the test, the calibration information 520 preferably influencing or specifying the control information 510. The calibration information 520 can be or can form the control information 510 or a part of the control information 510, even if this is not explicitly mentioned in the following.

The analysis device 200 can be calibrated and/or configured by calibration information 520 that can form part of the control information 510 or can be provided separately. For this purpose, the calibration information 520 can be determined, retrieved and/or transmitted to the analysis device 200 by means of the operating instrument 400.

In one example, fluid sensor calibration information 521 is provided which influences setting and/or evaluation of the fluid sensor 206A. The fluid sensor calibration information 521 is preferably dependent on the test to be carried out, the phase of the test and/or expected effects of a content change in a sensor portion 116 on the fluid sensor 206A during the test sequence, and/or contains various specifications which are dependent thereon.

Alternatively or additionally, tilt sensor calibration information 524 can be provided, preferably one or more threshold values 525, in particular a start threshold value 526 for blocking the start of a test if said threshold value is exceeded, and/or an interruption threshold value 527 for interrupting the test and/or for processing errors if said threshold is exceeded.

Alternatively, or additionally, sensor arrangement calibration information 528 can be provided, by means of which properties of the sensor arrangement 113 or sensor apparatus 113 are or can be set. In particular, it is provided that the sensor arrangement calibration information 528 is transmitted or can be transmitted to the sensor arrangement 113 or sensor apparatus 113 by the analysis device 200, and that the sensor arrangement 113 or sensor apparatus carries out or is designed to carry out a measurement taking into account the sensor arrangement calibration information 528.

The proposed analysis system 1 preferably includes evaluation information 530 which is stored in the database 500 and/or is retrievable or can be retrieved from the database 500. The evaluation information 530 is preferably designed to be able to interpret measurement results 713 that originate from the cartridge 100, in particular from the sensor apparatus 113.

The control information 510 and/or the evaluation information 530 particularly preferably includes instructions, preferably in the form of an algorithm and/or for controlling a process on or using a processor or controller. The instructions preferably form a module that can be or is implemented by the analysis device 200 and/or the operating instrument 400, as a result of which the behavior of the analysis device 200 and/or the operating instrument 400 can be or is changed.

The instructions are in particular commands, machine code, pre-compiled source code or source code. The instructions preferably form a module-like software component, in particular a plugin. The instructions can be designed to form and/or to replace a module of the operating instrument 400 and/or of the analysis device 200. For this purpose, the control information 510 and/or the evaluation information 530 can include a (software) interface for coupling or implementation by the control apparatus 207 and/or an evaluation module 440 of the operating instrument 400.

The control information 510 particularly preferably includes or forms a module of the control apparatus 207 that can be exchanged, preferably in terms of software. This module preferably contains instructions such as logic commands, loops and the like for controlling the test, in particular in the form of a computer program or computer program product to be executed by the analysis device 200 and/or the control apparatus 207. The control information 510 can be or form, in particular as a plugin, an exchangeable part of the control apparatus 207.

An evaluation module 440 is preferably formed by the operating instrument 400 or the operating instrument 400 includes the evaluation module 440. By means of the evaluation module 440, measurement results 713 read out from the sensor apparatus 113 are evaluated preferably using the evaluation information 530 and/or the evaluation module 440 is designed for this purpose.

The evaluation information 530 particularly preferably includes or forms a module of the evaluation apparatus 440 that can be exchanged, preferably in terms of software. This module preferably contains instructions such as logic commands, loops and the like for controlling the evaluation of measurement results 713, in particular in the form of a computer program or computer program product to be executed by the operating instrument 400 and/or the evaluation module 440. The evaluation information 530 can be or form, in particular as a plugin, an exchangeable part of the evaluation module 440.

Alternatively, or additionally, the instructions can include parameters for configuring the control apparatus 207 and/or the evaluation module 440. These parameters are preferably provided in addition to the instructions, for example for the analysis device 200 in the form of or including the calibration information 520. Alternatively, the control information 510 and/or evaluation information 530 can however also merely include parameters and/or other information for the control and/or evaluation.

The database 500 preferably includes a results memory 550 in which results can be stored and/or saved.

Within the meaning of the present invention, the term "database" should preferably be understood in a broad sense and also incorporates multi-part databases in particular. Therefore, in principle, the database 500 can be provided in different physical units or at different locations and/or can be composed of a plurality of subdatabases.

The operating instrument 400 can preferably be separated and/or disconnected from the analysis device 200 with respect to a data connection and/or physically. For this purpose, the analysis device 200 can initially be connected to the operating instrument 400 by the data connection DVA being established.

In order to control the test and/or the analysis device 200, the operating instrument 400 can retrieve control information 510 from the database 500 and transmit said information to the analysis device 200 in unaltered or altered form.

The operating instrument 400 is preferably designed to evaluate measurement results 713 which can preferably be generated by the sensor apparatus 113 of the cartridge 100 while the sample P is being tested. For this purpose, it is provided that measurement results 713, which can originate from a sensor apparatus 113 of the cartridge 100 and/or which can be transmitted from the analysis device 200 to the operating instrument 400, are or can be evaluated in the operating instrument 400. For this purpose, the operating instrument 400 can retrieve or receive the evaluation information 530 from the database 500 and, using this evaluation information 530, evaluate the measurement results 713, in particular in the evaluation module 440 of the operating instrument 400.

The operating instrument 400 preferably includes a memory 450. The memory 450 can be used to store, at least temporarily, control information 510, calibration information 520 and/or evaluation information 530, or the operating instrument 400 and the memory 450 can be designed for this purpose. Alternatively, or additionally, evaluation results 740, that have been or can be generated from the measurement results 713 by means of the operating instrument 400, can be stored in the memory 450.

In one example, the operating instrument 400 includes an output apparatus 410, preferably an in particular touch-sensitive screen or display 411 and/or a speaker 412. Alternatively or additionally, the operating instrument 400 includes an input apparatus 420, in particular a camera 421, a touchpad 422, a microphone 423 and/or a keyboard 424.

The operating instrument 400 is preferably designed to display on operating interface or a user interface via the output apparatus 410, in particular the screen or display 411, or to provide in another way operating elements for controlling the test and/or the analysis device 200, and/or to output a status or other information relating to the test. Alternatively, or additionally, commands can be received via the input apparatus 420, by means of which the operating instrument 400 starts, configures and/or controls the test of the sample P in a manner corresponding to the commands.

Preferably, the transmission of commands and/or information to the analysis device 200 is triggered via the input apparatus 420 or can be triggered by the input apparatus 420.

In particular, transmission of the control information 510 from the operating instrument 400 to the analysis device 200 can be initiated or controlled via the input apparatus 420. Alternatively, or additionally, the analysis device 200 can be controlled in order to receive the cartridge 100 and/or to start the test, preferably using the control information 510 and/or a command received via the input apparatus 420.

The operating instrument 400 is preferably designed to transmit, to the analysis device 200, control information 510 for receiving or ejecting the cartridge 100. In this case, a cartridge 100 can in particular be inserted only when the operating instrument 400 is connected to the analysis device 200, whereupon the operating instrument 400 can verify the cartridge 100 and can eject said cartridge or block a test if an error, such as incompatibility, is detected.

Alternatively, or additionally, the operating instrument 400 is designed to transmit control information 510 for starting the test to the analysis device 200. The test is thus preferably started only by a command originating from the operating instrument 400. The analysis device 200 itself preferably does not include a user interface for generating a start command or for causing the test to start. This task is preferably reserved for the operating instrument 400.

The cartridge 100 preferably includes at least one cartridge identifier 100C which corresponds to the cartridge 100 and/or to a batch with which the cartridge 100 is associated.

The cartridge identifier 100C is in particular a piece of information that is specific to the relevant cartridge 100, is in particular unique and/or is designed to uniquely identify the cartridge 100, such as an identification code which is assigned to the relevant cartridge 100 and makes it possible for said cartridge to be identified in a preferably unique manner.

Alternatively, or additionally, the cartridge identifier 100C makes it possible to assign the cartridge 100 to a production cycle and/or to a batch of particular cartridges 100. A batch is preferably characterized in that cartridges 100 are produced in the same continuous production cycle and/or are produced having the same components, in particular having the same sensor apparatuses 113 and/or the same reagents and the like. There is preferably a plurality of batches which can differ from one another with regard to production periods, batches of starting materials used and the like, for example.

The cartridge identifier 100C can be stored and/or saved in a memory means 100D of the cartridge 100. The memory means 100D can be a barcode 124, an NFC tag and/or a memory which is provided in the sensor apparatus 113, is connected to the sensor apparatus 113 or is assigned to the sensor apparatus 113, or another apparatus for storing code or the like.

The cartridge identifiers 100C are preferably assigned to the respective cartridges 100. In particular, the cartridge identifier 100C is formed by the cartridge 100, connected thereto and/or arranged thereon.

The analysis system 1 can include a plurality of cartridges 100 which can each preferably be distinguished from one another by means of at least one cartridge identifier 100C and/or which are assigned to a batch.

Alternatively, or additionally, the same cartridge 100 can include at least two cartridge identifiers 100C that each correspond to the cartridge 100. The cartridge identifiers 100C can preferably be read out by different read-out methods, in particular optically, by radio, by a wired connection or the like.

The respective cartridges 100 can include two different memory means 100D having the same or corresponding cartridge identifiers 100C. The memory means 100D are preferably independent of one another and/or separated from one another physically. The memory means 100D can preferably be read out in different ways, in particular electronically and/or by an electronic connection on the one hand, and wirelessly, in particular optically and/or by radio on the other hand.

Figure 4:
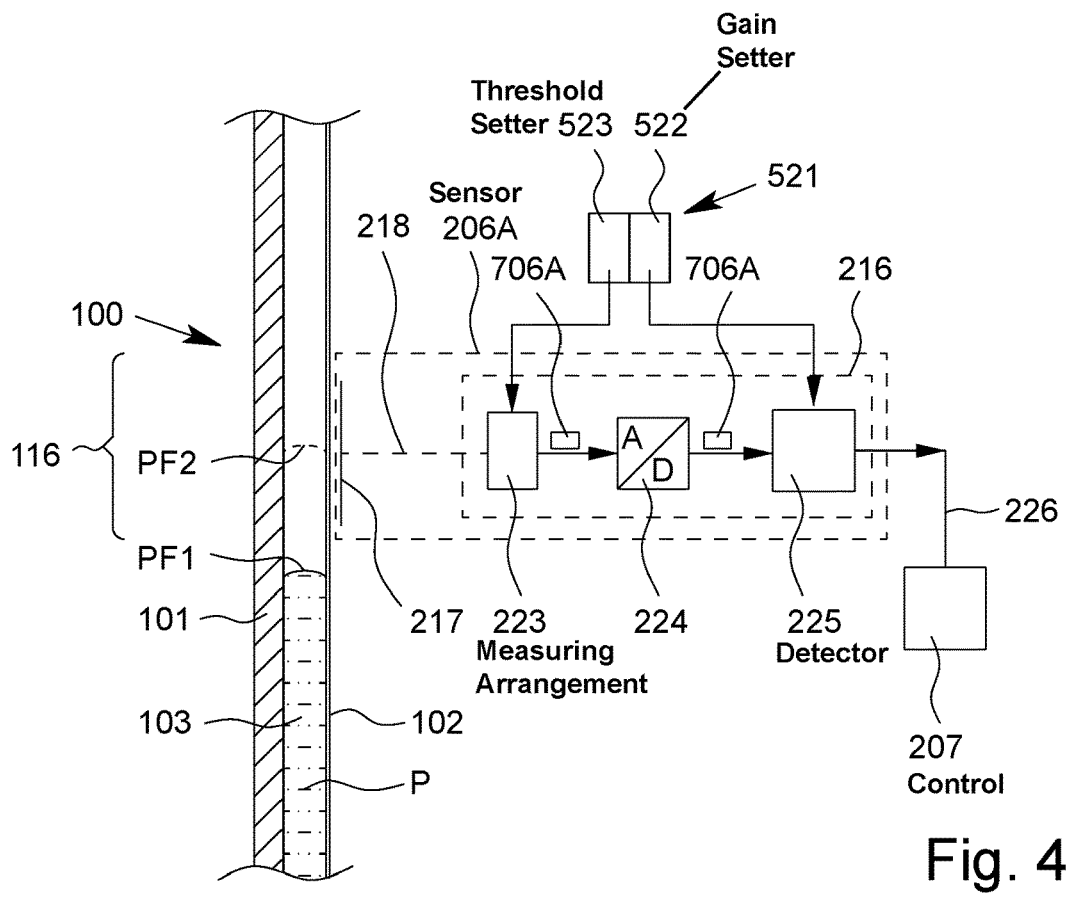
FIG. 4 is a schematic view of a proposed fluid sensor.

FIG. 4 is a schematic view of the fluid sensor 206A and a detail of the fluid system 103 of the cartridge 100 in the region of a sensor portion 116. However, the fluid sensor 206A can be realized independently of the fluid system 103, the analysis device 200 and the cartridge 100.

The sensor portion 116 can be formed by a cross-sectional widening of a channel 114 of the fluid system 103, as shown in FIG. 2 by way of example. In particular, it is provided that the inside diameter is larger than that of adjacent channels in the direction of the main plane of extension of the main body 101 of the cartridge 100 and/or transversely to a flow direction that is assigned to the sensor portion 116 and connects an inlet and an outlet of the sensor portion 116. This makes it possible for a liquid front PF1, PF2 to be formed that is wider and thus has a higher degree of detectability in comparison with adjacent channels 114.

The sensor portion 116 preferably includes (exactly) one inlet and (exactly) one outlet that have a preferably continuous and/or steady cross-sectional widening and/or cross-sectional tapering in order to prevent flow separations and/or turbulences. In principle, however, other constructions of the sensor portion 116 are also conceivable, although the described construction is preferred owing to a particularly high degree of detectability of content changes, in particular liquid fronts PF1, PF2.

In FIG. 4, the fluid system 103 includes a gas, in particular (conditioned) air or the like, in the sensor portion 116. Furthermore, the sample P or another liquid, which can be conveyed within the fluid system 103 of the cartridge 100, is located at other points in the fluid system 103. For details in this regard, reference is made to the description of FIGS. 1 and 2.

The sample P or another liquid that is located and/or can be conveyed in the fluid system 103 preferably includes or forms a boundary layer or front or liquid front PF1, preferably at a layer forming a boundary with the atmosphere in the fluid system 103 or with another fluid. The liquid front PF1 preferably extends at least substantially transversely to the flow direction and/or longitudinal extension of the sensor portion 116.

The liquid front PF1 can be moved within the fluid system 103 and/or within the sensor portion 116 by means of the sample P or the fluid that forms the liquid front PF1 being conveyed. In the example shown according to FIG. 4, the liquid front PF1 migrates into the sensor portion 116 by means of the sample P or another fluid being conveyed, and in the process displaces the gas or another fluid that was previously located in the sensor portion 116, as shown by the liquid front PF2 marked out with a dashed line.

The content of the sensor portion 116 is changed by the displacement. This content change in the sensor portion 116 can then be detected by the fluid sensor 206A.

Owing to the fact that the liquid front PF1, PF2 is continuously moving in the sensor portion 116 and through the sensor portion 116, a continual content change can preferably be determined and evaluated using the fluid sensor 206A.

The fluid sensor 206A preferably operates electrically. For this purpose, the fluid sensor 206A preferably includes a sensor electrode 217 which is preferably arranged in the analysis device 200, when the cartridge 100 is loaded, adjacently to the sensor portion 116 such that the electrical properties of the sensor electrode 217 are or can be influenced by the content of the sensor portion 116. In particular, the electrical properties are or can be changed by displacing the atmosphere and replacing it with the sample P or a liquid such that it is possible to identify that the liquid or sample P has reached the sensor portion 116.

Particularly preferably, the fluid sensor 206A operates capacitively. For this purpose, the sensor electrode 217 has a preferably plate-like or plate-shaped construction of which a flat side faces the sensor portion 116. On account of the sensor electrode 217 being arranged adjacently to the sensor portion 116, the ability of said sensor electrode 217 to absorb and store charges is dependent on the permittivity, in particular the relative permittivity, of the cartridge 100 and thus also on the content of the sensor portion 116. The fluid sensor 206A therefore detects the content change in the sensor portion 116 preferably indirectly on the basis of the change in the capacitance of the sensor electrode 217 resulting from a change in the permittivity of the content of the sensor portion 116.

The sensor electrode 217 optionally includes just one or exactly one pole, i.e. in particular exactly one sensor plate. This is advantageous in that a dedicated counter electrode does not need to be used. This simplifies the construction and arrangement of the fluid sensor 206A in complex systems in particular. However, a counter electrode can be used as well and is preferred in some embodiments discussed later and can be combined with the present embodiment as a counter electrode can be added (not shown).

The sensor electrode 217 is preferably designed to measure an electrical variable, in particular capacitance, which is dependent on an electrical property of the content of the sensor portion 116, said electrical property preferably being the permittivity, in particular the relative permittivity, of the content, which influences the electrical properties of the sensor electrode 217 and thus influences, preferably changes, the measurement result 706A.

Alternatively, or additionally, it is however also possible for the fluid sensor 206A to measure electrical conductivity of the content of the sensor portion 116. The change in the electrical conductivity of the content of the sensor portion 116 can be determined for example by electric and/or magnetic fields being coupled into the content of the sensor portion 116. Depending on the electrical conductivity, electrical currents are induced that are converted into heat in a manner dependent on the electrical conductivity, and this can be measured by the fluid sensor 206A, in particular as a loss. However, a fluid sensor 206A acting mostly based on variation of the capacitance of the sensor electrode 217 is preferred.

In principle, the fluid sensor 206A can, alternatively or additionally, also be operated inductively, the content change in the sensor portion 116 preferably being determined by so-called eddy current losses. Here too, the change in the electrical properties of the sensor electrode 217 is preferably determined depending on the content of the sensor portion 116, in particular depending on the electrical conductivity. This process preferably utilizes the fact that different conductivities of the content of the sensor portion 116 lead to different degrees of ability for inducing eddy currents and/or to different eddy current losses.

The term "eddy current loss" preferably denotes the effect whereby, when an eddy current is induced, owing to the finite electrical conductivity or the electrical resistance of the content of the sensor portion 116, energy is converted into heat energy and can be measured by the fluid sensor 206A as electrical energy loss.

The fluid sensor 206A preferably has evaluation electronics 216, in particular for detecting the content change in the sensor portion 116 of the cartridge 100 and/or for processing and/or evaluating the signal from the sensor electrode 217 or measurement result 706A.

The sensor electrode 217 is preferably connected to the evaluation electronics 216 by means of a sensor line 218.

The evaluation electronics 216 preferably includes a measuring arrangement 223. The measuring arrangement 223 can be designed to measure the electrical property that can be influenced by the content of the sensor portion 116, in particular the capacitance of the sensor electrode 217. Particularly preferably, the measuring arrangement 223 is designed to amplify a detected change in the electrical property of the sensor electrode 217 in order to be able to subsequently evaluate or interpret said change with a higher degree of accuracy.

The evaluation electronics 216, in particular the measuring arrangement 223, is preferably designed to carry out what is known as zero-point adjustment or offset adjustment. In this case, once the cartridge 100 has been loaded into the analysis system 200, the electrical property, in particular capacitance, of the arrangement including or formed by the sensor electrode 217 and the sensor line 218 is determined and/or compensated for in an initial state. In particular, this electrical property or capacitance is cancelled out in the evaluation electronics 216 by countermeasures and/or used as the zero point, in order for it to be possible to determine and/or output, on this basis, the slightest of changes in the electrical properties of the sensor electrode 217.

The evaluation electronics 216 preferably includes an analogue-to-digital converter 224, also referred to as an A/D converter 224. The A/D converter 224 converts the measuring signal (measurement result 706A), which is preferably initially present in the analogue form and which corresponds to the change in the electrical property of the sensor electrode 217 and indirectly to the content change in the sensor portion 116, into a digital signal. However, in principle, the A/D converter 224 can also be omitted and an evaluation can be carried out using analogue signals.

The analysis device 200 preferably includes a detection apparatus 225 for detecting the change in the electrical property of the sensor electrode 217. In the example shown, the detection apparatus 225 is formed by the evaluation electronics 216 or the evaluation electronics 216 includes the detection apparatus 225. In principle, the detection apparatus 225 can however also be formed so as to be separated from the evaluation electronics 216 and/or so as to be part of the control apparatus 207.

The detection apparatus 225 is preferably designed to evaluate the measurement result 706A in order to detect a content change in the sensor portion 116. Particularly preferably, the detection apparatus 225 analyzes a course or profile of or curve for the measurement result 706A and/or compares the measurement result 706A or a change thereof with a reference value.

The evaluation electronics 216 forwards the result of the evaluation by the detection apparatus 225 to the control apparatus 207 preferably via a control interface 226. The control apparatus 207 can control the test, in particular activate actuators, in a manner dependent on the content change in the sensor portion 116 being detected, in order to convey the sample P, to temperature-control the sample, to conduct the sample within the cartridge 100 in a certain way and/or to analyze the sample.

It is particularly preferably provided that the detection apparatus 225 transmits a signal to the control apparatus 207 via the control interface 226 as soon as a content change, in particular a content change in the sensor portion 116 that is expected or is in line with expectations in the test sequence, has been detected.

The control information 510 and/or execution information 511 can include condition information 511C which is designed to control the test in a particular manner dependent on the event of the signal being transmitted and/or the content change being identified.

In one aspect of the present invention, which can also be implemented independently, it is provided that the detection apparatus 225 is configured and/or that the configuration is changed depending on a measurement result 706A expected in the test sequence. In particular, the detection apparatus 225 compares the measurement result with a reference value and/or threshold value 522 which is or can be set and/or is or can be specified in a manner dependent on the cartridge 100, the test to be carried out and/or the phase of the test. This makes it possible to fix, define or adapt the reference value and/or threshold value 522 for a content change that is expected or is to be expected.

In particular, the analysis system 1 includes a plurality of different cartridges 100, supports a plurality of different cartridges 100 and/or supports a plurality of different tests. In the same or different tests, test phases and/or test steps, it can be provided that different substances, preferably liquids, in particular samples P, wash buffers, reagents, etc., are conveyed within the fluid system 103, which substances influence the electrical properties of the sensor electrode 217 in different ways, in particular sometimes to a greater extent and sometimes to a lesser extent, when they reach the sensor portion 116. This can be taken into account by the detection apparatus 225, particularly preferably by different reference values and/or threshold values 522 being used or by the reference value and/or threshold value 522 being changed or adapted.

It is also possible for different content changes to be provided during a test using the same cartridge 100, for example when different substances, such as the sample P, wash buffer, reagents, gases and the like, arrive at the sensor portion 116 alternately and/or in succession.

During the test, at least two, preferably at least three or more, different measurement results 706A are therefore expected. Consequently, the reference value and/or threshold value 522 can be fixed, defined and/or adapted preferably such that each of the expected content changes in the sensor portion 116 can be detected reliably and/or with an improved degree of accuracy. This does not mean that, in this case, the fluid sensor 206A determines the content of the sensor portion 116, even though this would also be possible in principle, but rather it means that the sensitivity, thresholds and the like for the sensor electronics 216 can be adapted in order to improve reliable detection of a content change.

As an alternative or in addition to the reference value and/or threshold value 522, the gain 523 of the measuring arrangement 223 can be set, specified and/or varied, it being possible for the criteria and procedures therefor to correspond to the specification and/or adaptation of the reference value and/or threshold value 522, and so reference is made to corresponding explanations.

The fluid sensor calibration information 521 preferably includes the reference value and/or threshold value 522 and/or the gain 523 and/or one or more of an amplitude, a frequency, a period length, a duty cycle and a pulse length of an AC source 216B discussed later on referring to FIG. 12 to 15.

It is not mandatory that the fluid sensor 206A has a variable gain, variable threshold and/or a variable AC source 216B. However, it is preferred that the fluid sensor 206A has at least one variable component, which, preferably, can be configured/calibrated, in particular by means of the fluid sensor calibration information 521.

As already explained in conjunction with FIG. 3, the fluid sensor calibration information 521, in particular the reference value and/or threshold value 522 and/or the gain 523 and/or one or more of an amplitude, a frequency, a period length, a duty cycle and pulse length of the AC source 216B, can be retrieved and/or transmitted, in particular sent, to the analysis device 200. For this purpose, the fluid sensor calibration information 521 can be retrieved from the database 500 and/or transmitted to the analysis device 200 by means of the operating instrument 400.

In this respect, it is particularly preferable for in particular the operating instrument 400 to determine or establish the cartridge identifier 100C of the cartridge 100, in particular to read out said identifier 100C, for example from the barcode 124 of the cartridge 100 using the camera 421.

Using the cartridge identifier 100C, the operating instrument 400 and/or the database 500 can identify the fluid sensor calibration information 521 corresponding to the cartridge 100 and/or a test that can be carried out using the cartridge 100, and transmit said information to the analysis device 200. The fluid sensor calibration information 521 can form part of the control information 510 and/or the calibration information 520.

As described in conjunction with FIG. 3, the fluid sensor calibration information 521 can therefore be retrieved or transmitted as part of the control information 510. However, in principle, it is conceivable for the fluid sensor calibration information 521 to also be handled separately from the control information 510.

In particular, the control information 510 contains calibration information 520, i.e. in particular the fluid sensor calibration information 521, as part of execution information 511, and therefore, when the test is being carried out, the reference value and/or threshold value 522 and/or the gain 523 and/or one or more of an amplitude, a frequency, period length, a duty cycle and pulse length of the AC source 216B can be adapted on the basis of the control information 510.

In general, it is therefore preferable for the sensitivity of the evaluation electronics 216 to be specified and/or changed using the calibration information 520 depending on the selection of one of a plurality of possible cartridges 100 and/or depending on the selection of a specific test and/or the phase of a test sequence, the calibration information 520 in particular being established, determined, retrieved and/or used on the basis of the cartridge identifier 100C.

The fluid sensor 206A does not need to be calibrated and/or does not need to be able to be calibrated. Accordingly, aspects described herein that are not necessarily related to calibration of the fluid sensor 206A and, in particular discussed in the following section, can thus be realized independently thereof, i.e., without calibration, even if calibration capability can be provided, combined and particularly advantageous.

Figure 5:
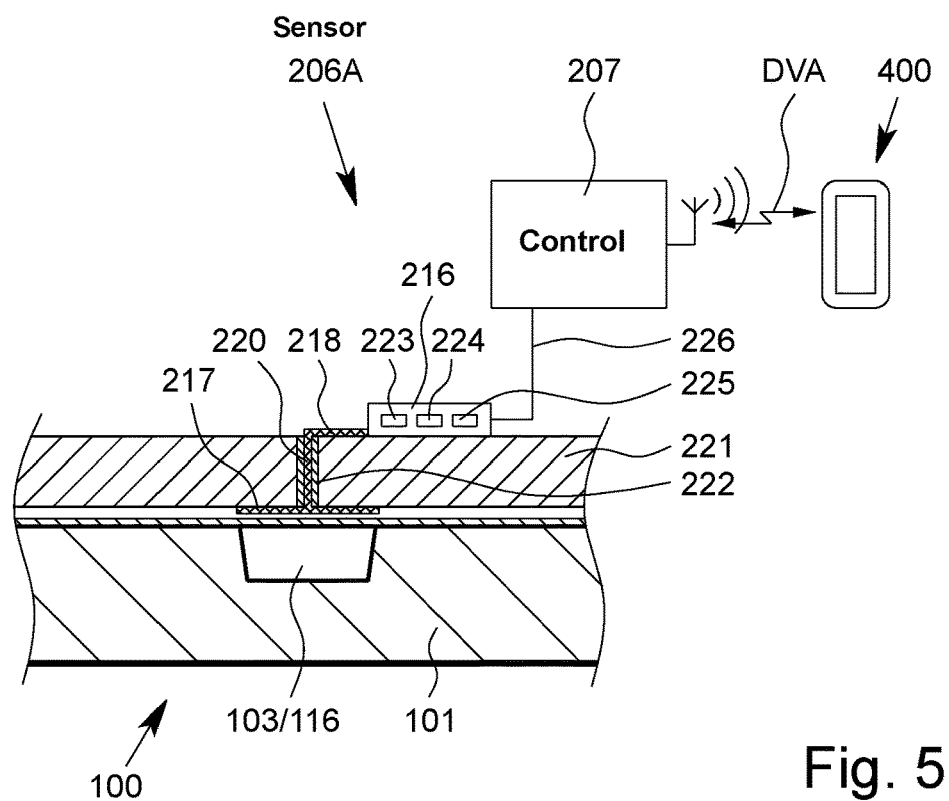
FIG. 5 is a schematic section through the proposed fluid sensor.

FIG. 5 is a schematic section through the fluid sensor 206A and a detail of the cartridge 100 that includes the main body 101 which forms the fluid system 103, in this case in the region of the sensor portion 116.

The sensor electrode 217 is arranged adjacently to the sensor portion 116 such that the content or a content change in the sensor portion 116 can be detected by means of the fluid sensor 206A.

The sensor electrode 217 is connected to the evaluation electronics 216 by means of the sensor line 218.

Preferably, only one sensor electrode 217 is provided, i.e. what is known as a single-ended arrangement that does not include a counter electrode. In principle, other solutions are also possible. In a preferred alternative, a counter electrode is provided next to the sensor electrode 217.

The sensor line 218 preferably includes a via 220 in a printed circuit board 221 of the analysis device 200. The evaluation electronics 216 is preferably arranged on a side of the printed circuit board 221 that is remote from the sensor electrode 217. This provides, in a simple manner, for a construction or design that is at least substantially flat or planar on the side of the printed circuit board 221 that faces the cartridge 100, the construction being advantageous for positioning the printed circuit board 221 flat against the cartridge 100 and/or for effective coupling of the sensor electrode 217 to the cartridge 100.

The evaluation electronics 216 is preferably provided in a housing, in particular in a dual in-line package housing, an SMD housing and/or a BGA housing. In this case, the evaluation electronics 216, including the housing, is arranged on the side of the printed circuit board 221 that is remote from the sensor electrode 217. This is advantageous in terms of construction in that the evaluation electronics 216 does not increase the distance between the sensor electrode 217 and the cartridge 100.

The sensor line 218 is preferably surrounded by a dielectric 222 in the region of the via 220. The dielectric 222 can be arranged or provided next to, preferably around, the sensor line 218, in particular in the manner of a sleeve. The dielectric 222 can be separated from the printed circuit board 221 and/or can be formed by the printed circuit board 221. The dielectric 222 of the via 220 are optional and might or might not be realized.

Figure 6:
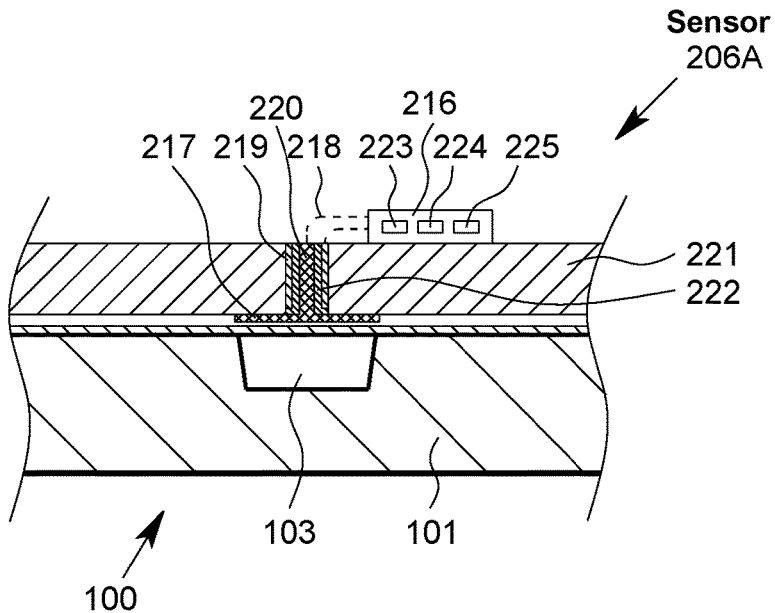
FIG. 6 is a schematic section through an alternative embodiment of the proposed fluid sensor.

FIG. 6 shows an alternative, preferred embodiment of the proposed fluid sensor 206A, again in a schematic section, a shield electrode 219 being assigned to the sensor line 218. In particular, the shield electrode 219 extends adjacently to the sensor line 218. This makes it possible to prevent interfering signals from being coupled into the sensor line 218.

Alternatively, or additionally, the shield electrode 219 reduces the influence or influenceability of the capacitance and/or capacitor formed by the sensor electrode 217 and the sensor line 218 in the region of the sensor line 218. This can be achieved by the shield electrode 219 forming, together with the sensor line 218, an at least substantially invariable and/or constant electrical capacitance. Influences on the evaluation of the measurement results 706A that could potentially lead to an incorrect interpretation, arising as a result of the capacitance of the arrangement, consisting of the sensor electrode 217 and the sensor line 218, when there is a change in the properties of the surroundings at a greater distance than the distance between the sensor line 218 and the shield electrode 219, are thus prevented.

Figure 7:
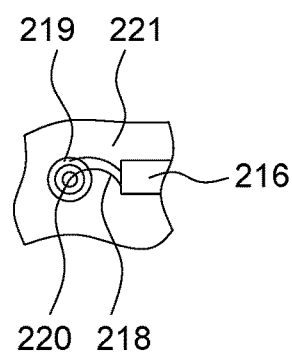
FIG. 7 is a schematic top view of the alternative embodiment according to FIG. 6.

The shield electrode 219 is preferably electrically connected to the evaluation electronics 216 and/or to electrical ground. This can be achieved for example by lines provided on the printed circuit board 221. Alternatively, or additionally, wires, for example bonding wires, can be used, as is shown by way of example in the very schematic detail from FIG. 7.

The shield electrode 219 can optionally surround the sensor line 218 in the region of the via 220, in particular in the manner of a sleeve. In order to prevent direct electrical, i.e. galvanic, contact between the shield electrode 219 and the sensor line 218, the dielectric 222 is preferably provided therebetween. The shield electrode 219 is therefore preferably always isolated from the sensor line 218. The dielectric 222 or any shielding coaxial shield electrode 219 of the via 220 are optional and might or might not be realized.

The sensor electrode 217 according to FIG. 6 is arranged directly on the printed circuit board 221. In particular, the sensor electrode 217 is formed and/or structured by structuring a metal lamination of the printed circuit board 221, in particular a copper lamination. This makes it possible for the sensor electrode 217 to have a planar construction.

Figure 8:
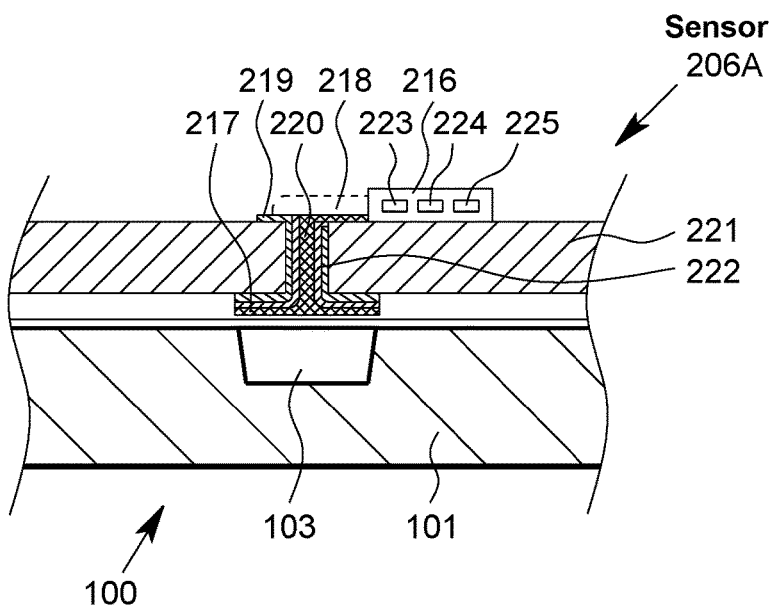
FIG. 8 is a schematic section through another alternative embodiment of the proposed fluid sensor.

FIG. 8 shows another variant of the fluid sensor 206A, the shield electrode 219 being guided in parallel with the sensor electrode 217 on the side facing the cartridge 100. In this case, the sensor electrode 217 preferably has a multilayered construction, the sensor electrode 217 in particular being provided on a side of the dielectric 222 that faces the cartridge 100 and the shield electrode 219 in particular being provided on a side of the dielectric 222 that is remote from the cartridge 100. The dielectric 222 or any shielding coaxial shield electrode 219 of the via 220 are optional and might or might not be realized.

Figure 9:
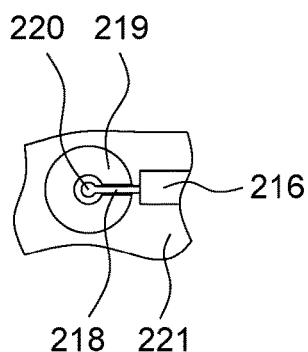
FIG. 9 is a schematic top view of another alternative embodiment of the proposed The fluid sensor according to FIG. 8.

As shown in the very schematic top view according to FIG. 9, the shield electrode 219 can cover the sensor electrode 217 on the side that is remote from the cartridge 100, preferably at least substantially completely and/or in a projecting manner.

Furthermore, the shield electrode 219 is preferably guided on the printed circuit board 221, in particular at a short distance from and/or at least substantially in parallel with the sensor line 218. The sensor line 218 is preferably formed as a conducting track on the printed circuit board 221. The shield electrode 219 is also preferably formed on the printed circuit board 221 at least in part. This can be achieved by the metal surface or lamination of the printed circuit board 221 being structured in a corresponding manner.

The sensor line 218 and the shield electrode 219 extend on the printed circuit board 221, in particular on the flat side thereof that is remote from the cartridge 100, preferably in the same plane and/or next to one another.

In order to prevent galvanic contact between the sensor line 218 and the shield electrode 219, the shield electrode 219 can surround the sensor line 218 in the region of the via 220 and be guided, preferably in an uninterrupted manner, between the via 220 and a connection point for the sensor electronics 216 so as to be adjacent and/or parallel to the sensor line 218.

In the region of the via 220, the shield electrode 219 is preferably arranged coaxially with the sensor line 218. However, it is not absolutely necessary for the shield electrode 219 to completely surround the sensor line 218.

Figure 10:
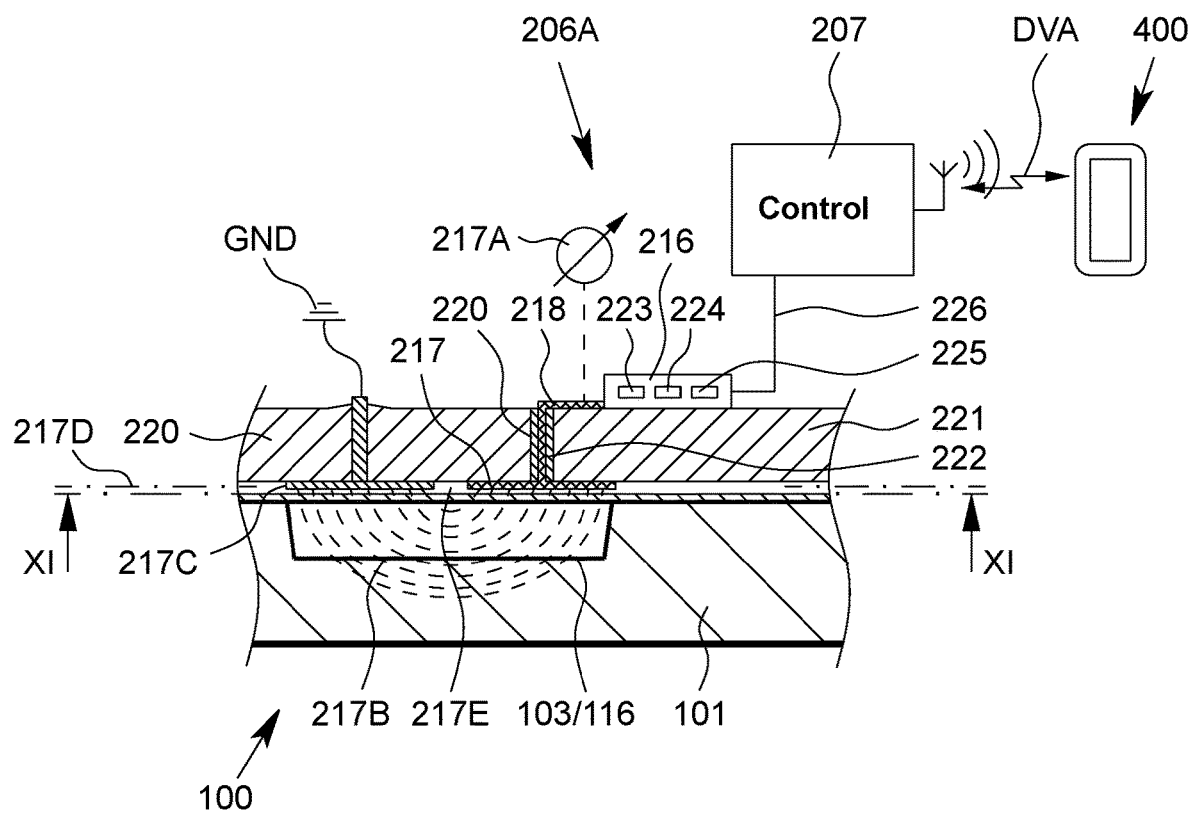
FIG. 10 is a schematic section through the proposed fluid sensor having a sensor electrode and a counter electrode.

FIG. 10 is a schematic view of the fluid sensor 206A and of a detail of the fluid system 103 of the cartridge 100 in the region of the sensor portion 116. In order to avoid repetitions, in the following the focus is on differences and further aspects compared to the previously described embodiments, and the disclosure regarding the previously described embodiments applies in addition and vice versa as far as appropriate.

The sensor electrode 217 has an electrode potential 217A. The difference between the electrode potential 217A and ground potential is called (sensor) electrode voltage $U_{SE}$. As the ground potential remains unchanged, the terms "electrode potential" and "electrode voltage" are used synonymously and can be replaced by one another.

The sensor electrode 217 has or produces an electrical field 217B or is configured to do so. The electrical field 217B passes the sensor portion 116 when the sensor electrode 217 and the sensor portion 116 are facing towards each other in their operating position. This operating position is characterized in the present embodiment by cartridge 100 being received in the analysis device 200. However, the fluid sensor 206A can be used in different arrangements as well. Thus, the fluid sensor 206A forms an independent aspect and can be realized independently, but can advantageously be used or combined with a cartridge 100 based analysis system 1 as previously described.

The electrical field 217B depends on the electrical properties of the content of the sensor portion 116. In particular, an empty sensor portion 116 or a sensor portion filled with air, protective gas or different gaseous substances cause a different influence on the electrical field 217B than a liquid like water or a sample P.

In the example shown in FIG. 10, the sensor electrode 217 has a counter electrode 217C such that the electrical field 217B is arranged or produced primarily or at least to a significant extend between the sensor electrode 217 and the counter electrode 217C. However, there can be at least one of a shield electrode, a ground plane and parasitic capacitances causing part of the total capacitance value of the sensor electrode 217 as well.

In the example depicted in FIG. 10, a shield and/or ground layer 219A is arranged between the sensor electrode 217 and the evaluation electronics 216. This allows shielding the sensor electrode 217 from fields that might be caused by the evaluation electronics 216 or other potential sources of disturbance.

The shield and/or ground layer 219A can be arranged more than 0.5 mm, preferably more than 0.8 mm, and/or less than 2 mm, preferably less than 1.6 mm, particularly preferably about 1.2 mm, from the sensor electrode 217 or its plane 217D.

The shield and/or ground layer 219A and the sensor electrode 217 preferably is arranged on different sides of the printed circuit board 221. This allows to reduce the capacitance between the sensor electrode 217 and the shield and/or ground layer 219A such that the capacitance between them is reduced or minimized. Accordingly, a share of the capacitance value of the sensor electrode 217 which is fixed can be minimized and/or a share of the capacitance value of the sensor electrode 217 which varies depending on the permittivity of the content of the sensor portion 116 is maximized. This allows improving the sensitivity of the fluid sensor 206A.

The shield and/or ground layer 219A can be realized by one layer of a multi-layer printed circuit board 221. The shield and/or ground layer 219A preferably is a ground plane. The via 220 preferably extends through the shield and/or ground layer 219A without having direct electrical or galvanic contact to the shield and/or ground layer 219A.

In the example shown, the shield and/or ground layer 219A includes a hole through which via 220 extends. Apart from that hole, the shield and/or ground layer 219A preferably forms a continuous conductive layer in the area between the sensor electrode 217 and the sensor electronics 216.

The shield and/or ground layer 219A preferably is connected to ground.

The counter electrode 217C preferably is connected to ground and/or to a potential having a behavior complementary to that of the potential of the sensor electrode 217 to form a differential operation.

The counter electrode 217C in the example shown is connected to the shield and/or ground layer 219A. Alternatively or additionally, the shield and/or ground layer 219A forms the counter electrode 217C.

The via 220 of the embodiment shown in FIG. 10 optionally can have one or more features discussed referring to FIGS. 5 to 9 even if not mandatory and depicted.

Preferably, the sensor electrode 217 and the counter electrode 217C are arranged side-by-side. In the embodiment shown in FIG. 10, the sensor electrode 217 and the counter electrode 217C have at least essentially parallel edges in a direction corresponding to or being parallel to a course of the sensor portion 116 or of a main flow direction defined by the shape of the sensor portion 116. Accordingly, a liquid front PF1, PF2 will at least basically move along this direction when a liquid, in particular a sample P, enters the sensor portion 116.

The sensor electrode 217 preferably is coupled directly to the evaluation electronics 216 discussed later referring to FIGS. 12 and 13 via the shield and/or ground layer 219A. A sensor line 218 can be provided to realize this connection. The sensor line 218 preferably is a strip of conductive material, preferably extending parallel to the ground plane and/or forming an electrical transmission line, in particular a so called microstrip.

In one further aspect of the present invention, which can be realized independently as well, the counter electrode 217C can function to shield the sensor electrode 217 from channels 114 being arranged in the surrounding area of the sensor portion 116. In particular, the counter electrode 217C is arranged to face towards a channel 114 of the cartridge 100 which is closest to the sensor portion 116. This helps to avoid potential disturbances resulting from events happening in the closest channel 114.

The sensor electrode 217 and the counter electrode 217C preferably are arranged side by side (one left one right of a projection of a central main flow direction within the sensor portion 116 perpendicular to the extension of the main body 101 or the cover 102 or a plane, in which the channels 114 are arranged) the such that the gap 217E dividing the sensor electrode 217 and the counter electrode 217C form one another is arranged centrally over the sensor portion 116. It can be determined, which channel 114, which differs from the sensor portion 116, is the closest to the gap 217E, in particular has a minimum distance measurable perpendicular to the flow direction of the sensor portion 116.

The gap 217E preferably is configured to maximize the electrical field in the volume under the electrodes 217, 217C, i.e. at a side facing towards the cartridge 100 or facing away from the printed circuit board 221. This improves the sensitivity of the fluid sensor 206A.

Figure 11:
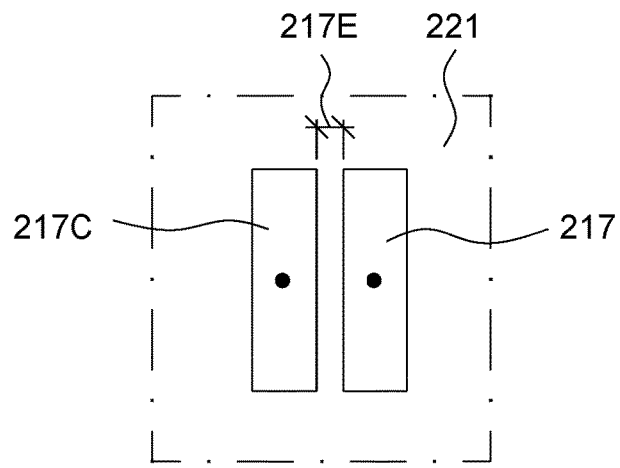
FIG. 11 is a schematic top view of the sensor electrode and the counter electrode of the fluid sensor according to FIG. 10.

FIG. 11 shows a sectional view of the fluid sensor 206A according to FIG. 10 along cutting line XI-XI of FIG. 10. In FIG. 11, the sensor electrode 217 and the counter electrode 217C are depicted in a top view. In the example shown, the sensor electrode 217 and the counter electrode 217C are arranged on the printed circuit board 221. However, this is not mandatory.

The sensor electrode 217 and the counter electrode 217C in the example shown are placed in a common plane 217D. This is preferred as this enables good sensitivity of the fluid sensor 206A while a different or alternative counter electrode placed on a side of the cartridge 100 facing away from the sensor electrode 217 is not necessary but optionally can be realized alternatively or in addition. Placing the sensor electrode 217 and the counter electrode 217C on the same side of the cartridge 100 next to each other provides the advantage that long signal ways all around the cartridge 100 and, thus, potential parasitic effects are avoided and a very compact and reliable structure is provided.

As can be seen in FIG. 11, the sensor electrode 217 and the counter electrode 217C have similar forms and/or elongated shapes with the same or a similar extension and/or being at least basically parallel.

The electrodes 217, 217C might extend more than 1 mm, preferably more than 2 or 3 mm, and/or less than 20 mm, preferably less than 10 or 18 mm, in particular at least essentially 5 mm, in flow direction. Alternatively, or additionally, the electrodes 217, 217C preferably extend at least essentially along the complete sensor portion 116 or a widening characterizing the sensor portion 116. Alternatively, or additionally, the electrodes 217, 217C might extend more than 0.3 mm, preferably more than 0.5 or 0.8 mm, and/or less than 2 mm, preferably less than 1.8 or 1.4 mm, in particular at least essentially 1 mm, perpendicular to flow direction. This might be subject to changes depending on the application.

Between the sensor electrode 217 and the counter electrode 217C there is a gap 217E.

The gap 217C might extend more than 0.3 mm, preferably more than 0.5 or 0.8 mm, and/or less than 2 mm, preferably less than 1.8 or 1.4 mm, in particular at least essentially 1 mm. the gap 217C might have similar extensions and/or a similar shape as one or more of the electrodes 217, 217C.

The gap 217E preferably is chosen such that the electrical field 217B apart of parasitic capacitances and capacitances to a shield or ground extends primarily or is able to extend primarily through the sensor portion 116, through a majority of the cross section of the sensor portion 116, the majority of the width and/or depths of the sensor portion 116.

This gap 217E preferably is smaller than a width of the sensor portion 116, which is a clear span between the side walls of the sensor portion 116 and/or perpendicular to the flow direction as defined by the sensor portion 116. Preferably, the gap 217E is less than half of the width of the sensor portion 116.

Alternatively or additionally, the gap 217E is more than 50% and/or less than 150% of the height of the sensor portion 116, which is a clear span of the sensor portion for leading liquid/the sample P perpendicular to the plane 217D, in which at least the sensor electrode 217 and/or the counter electrode 217C and/or the gap 217E is or are arranged.

However, differently shaped sensor electrodes 217 and/or counter electrodes 217C are possible as well.

The sensor electrode 217 is connected to the measuring arrangement 223. Preferred schematics of the measuring arrangement 223 together with the sensor electrode 217 are depicted in FIGS. 12 and 13. Those measuring arrangements 223 as well as the fluid sensor 206A having such sensor arrangements 223 form an independent inventive concept of the present invention and can be realized independently of the analysis system 1, the cartridge 100 and the analysis device 200. However, a combination is particularly preferred and advantageous.

The fluid sensor 206A according to the present aspect is configured for detecting a content change in the sensor portion 116 of the fluid system 103 or a different fluid system not shown. Accordingly, reference is made to the fluid system 103 described before although this fluid system 103 is not required for the fluid sensor 206A.

The fluid sensor 206A particularly preferably is configured to detect a liquid front PF1, PF2 in the sensor portion 116 when such liquid front PF1, PF2 is arranged in the sensor portion 116, enters the sensor portion 116 and/or passes the sensor portion 116 and/or exits the sensor portion 116, thus, causing the content of the sensor portion 116 and/or its permittivity to change.

The fluid sensor 206A includes at least the sensor electrode 217, and, preferably, the counter electrode 217C as previously described or realized differently.

The sensor potential 217A of the sensor electrode 217 preferably is the electric potential of a node 216I being directly electrically connected with a surface of the sensor electrode 217 being arranged for facing towards the sensor portion 116.

The sensor electrode 217 has a capacitive behavior. Thus, the sensor electrode 217 is capable to store electrical energy in the electrical field 217B formed by the sensor electrode 217 when being charged, i.e., when the sensor electrode 217 receives charge carriers causing the electrical field 217B to change and/or a charge to change and/or the electrode potential 217A (sensor electrode voltage $U_{SE}$) to change accordingly.

The sensor electrode 217 is or can be charged by a current of charge carriers caused by or provided by the AC source 216B. Adding charge carriers to the sensor electrode 217 causes the charge and/or electrode potential 217A (sensor electrode voltage $U_{SE}$) to change accordingly. As the AC source 216B preferably is a voltage source, its voltage causes the current until the sensor potential 217A (sensor electrode voltage) or a sum of the sensor potential 217A (sensor electrode voltage $U_{SE}$) and a voltage drop of the UED 216A approaches or reaches the amplitude $U_{AC}$, alternatively called peak, of the AC source 216B.

The sensor electrode 217 has a capacitance value being indicative of a capability to store charge carriers. The capacitance value can be expressed in pF. The capacitance value defines a ratio of a change of the electrode potential 217A and a number of charge carriers added to the sensor electrode 217 or removed from the sensor electrode 217 during charge to change of the electrode potential 217A (sensor voltage $U_{SE}$). This capacitance value in an operating position of the sensor electrode 217 relative to the sensor portion 116 depends on the content of the sensor portion 116 and, thus, varies when the content changes to a content of a different electrical permittivity. Thus, the fluid sensor 206A according to the present invention preferably is configured to sense changes in the electrical permittivity of the sensor portion 116, in particular but not mandatorily caused by a content change effecting a change in the permittivity of the sensor portion 116.

The fluid sensor 206A, in particular the evaluation electronics 216, and more specifically the measuring arrangement 223, includes a uni-directional electrical device, in the following referred to as UED 216A. This UED 216A particularly preferably is realized by a diode. More generally, the UED 216A is a device or circuit enabling current flow in one direction and blocking current flow in the opposite direction.

Further, the fluid sensor 206A, in particular the evaluation electronics 216 and specifically preferably the measuring arrangement 223, further includes the AC source 216B. The AC source 216B preferably provides a voltage (amplitude) $U_{AC}$.

The AC source 216B particularly preferably it a pulse source. However, the AC source 216B alternatively or additionally can be a different source for providing an alternating voltage or current, preferably a periodic one.

The AC source 216B can be variable with regard to one or more of an amplitude, a frequency, period length, a duty cycle and pulse length. The AC source 216B can be configurable or configured regarding one or more of an amplitude, a frequency, period length, a duty cycle and pulse length, preferably by means of fluid sensor calibration information 521 or differently.

Alternatively, or additionally, the A/D converter 224 and/or the detection apparatus 225, in particular at least one reference voltage and/or threshold thereof, can be configurable or configured, preferably by means of fluid sensor calibration information 521 or differently.

The AC source 216B is coupled via the UED 216A to the sensor electrode 217 to charge the sensor electrode 217. In the embodiment depicted in FIG. 12, the UED 216A connects the AC source 216B to the sensor electrode 217 such that charge carriers from the AC source 216B can be transferred to the sensor electrode 217 in order to charge the sensor electrode 217 while the UED 216A blocks transfer of charge carriers from the sensor electrode 217 back towards the AC source 216B. In other words, the UED 216A enables a current flow from the AC source 216B and blocks a current flow back to the AC source 216B.

The AC source 216B preferably charges or is configured to charge the sensor electrode 217 to a sensor potential 217A which is a voltage drop of the UED, in particular a diode voltage drop, below the amplitude (peak) $U_{AC}$ of the AC source 216B.

Further, the evaluation electronics 216 includes a discharge path 216C. The discharge path 216C enables charge carriers to flow (drain) from the sensor electrode 217 such that the electrode potential 217A changes.

This discharge path 216C preferably is realized independently of the AC source 216B. Accordingly, the discharge process is achieved by the discharge path 216C without the AC source 216B being involved. This in the present embodiment is realized by the UED 216A which blocks any discharge of the sensor electrode 217 via the UED 216A and, thus, via the AC source 216B.

In conclusion, the UED 216A is configured to enable charging the sensor electrode 217 via the UED 216A while the UED 216A is configured to block discharging the sensor electrode 217 via the UED 216A.

Use of the UED 216A enables discharging the sensor electrode 217 via the discharge path 216A in a predictable manner such that the course of the electrode potential 217A in a predictable manner depends on the capability of the sensor electrode 217 to store charge carriers, i.e. from the capacitance value and, thus, from the permittivity of the content of the sensor portion 116.

While the AC source 216B in combination with the UED 216A acts as a charging means merely for charging the sensor electrode 217, the discharge path 216C causes afterwards discharge of the sensor electrode 217 resulting in a course of the electrode potential 217A which is indicative of (the permittivity) of the content of the sensor portion 116 or a change thereof.

The discharge path 216C preferably couples the sensor electrode 207 with a reference potential 216D. The reference potential 216D can be defined by a source relative to ground or can be ground.

The discharge path 216C preferably includes a first coupling element 216E, preferably a resistor, through which charge carriers from the sensor electrode 217 can flow to discharge the sensor electrode 217.

At least via the first coupling element 216E the sensor electrode 207 is preferably continuously charged/chargeable or discharged/dischargeable when the electrode potential 217A differs from the reference potential 216D, thus causing the electrode potential 217A to approximate the reference potential 216D. This can be realized differently, and examples are discussed later on with reference to FIGS. 12 and 13.

The fluid sensor 206A preferably includes an electrical filter 216F. The electrical filter 216F particularly preferably is or includes a lowpass filter. Alternatively or additionally, the electrical filter 216F is configured to smoothen and/or to integrate the course of the electrode potential 217A. The electrical filter 216F for that purpose preferably is coupled to the sensor electrode 217. The electrical filter 216F is configured to form a measurement result 706A based on the course of the electrode potential 217A.

Figure 12:
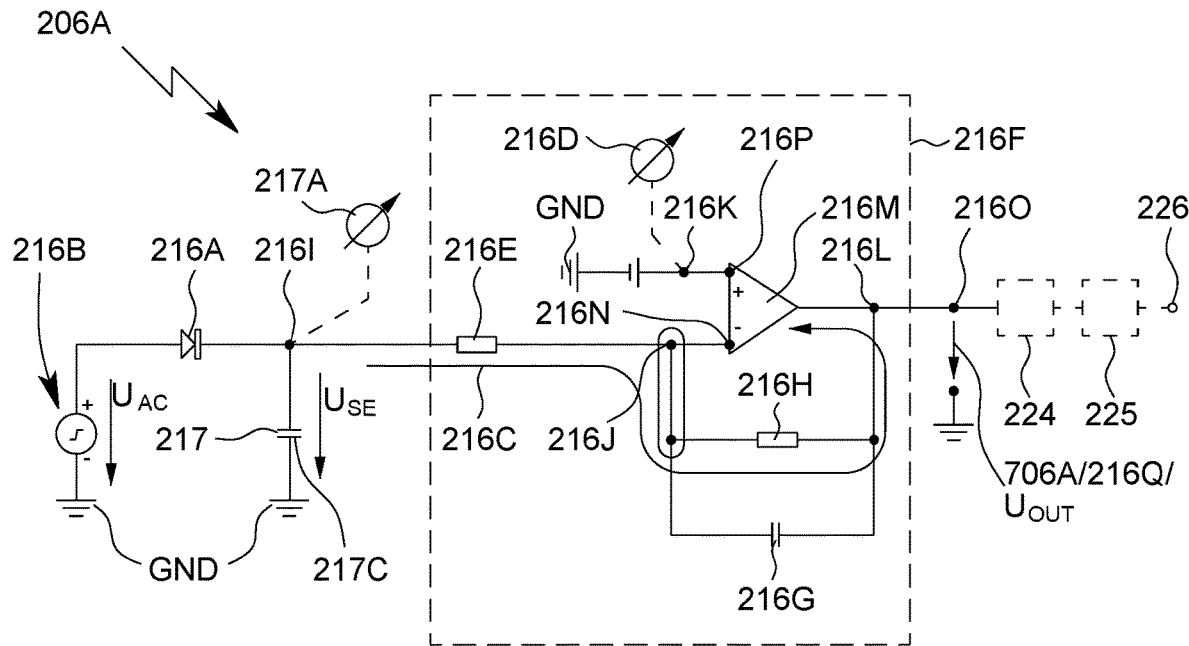
FIG. 12 is a schematic of a circuit of the evaluation electronics.
Figure 13:
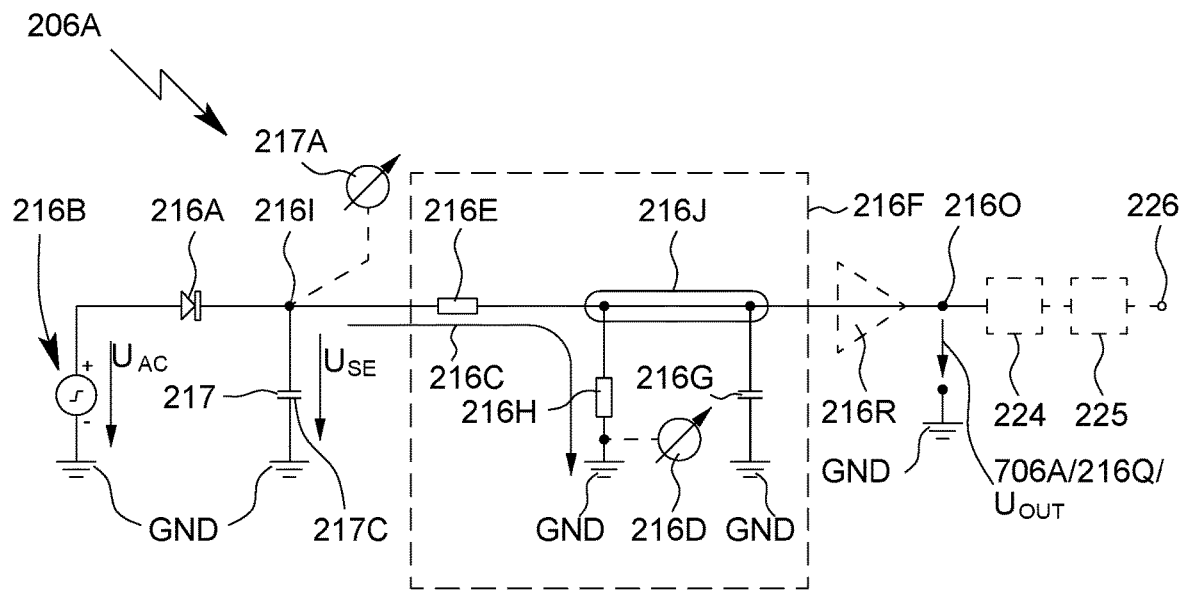
FIG. 13 is a schematic of an alternative circuit of the evaluation electronics.

In the preferred embodiments depicted in FIGS. 12 and 13, the electrical filter 216F includes a charge carrier storage, preferably realized as capacitor 216G. This a charge carrier storage or capacitor 216G is coupled to the sensor electrode 217 via the first coupling element 216E. Thus, the first coupling element 216E both forms the discharge path 216C or a part thereof, and defines or influences the filter function of the electrical filter 216F.

The discharge path 216C preferably includes a second coupling element 216H which is (directly) coupled with the first coupling element 216E and, preferably, with capacitor 216G. Thus, the first coupling element 216E and the second coupling element 216H and the charge carrier storage/capacitor 216G are directly coupled in a common node 216J. The second coupling element 216H couples the first coupling element 216E with a reference node 216K which is at a reference potential 216D. The reference potential 216D can be ground or different at least essentially constant potential.

The fluid sensor 206A in the example shown in FIG. 12 has an electrical filter 216F which is realized actively. The active electrical filter 216F in the embodiment shown in FIG. 12 includes an operational amplifier 216M, preferably forming the measuring arrangement 223. The operational amplifier 216M preferably is arranged to realize a low path filter and for an amplification of the sensor voltage $U_{SE}$ which is a difference between the electrode potential 217A and a reference voltage like ground.

In the embodiment shown in FIG. 12 an inverting input 216N of the operational amplifier 216M is coupled with the sensor electrode 217 via the first coupling element 216E. An output 216O of the operational amplifier 216M is fed back (coupled) to the inverting input 216N of the operational amplifier 216M via the capacitor 216G and the second coupling element 216H, a charge carrier storage/capacitor 216G and the second coupling element being connected in parallel. The reference potential 216D is provided to a non-inverting input 216P of the operational amplifier 216M.

The operational amplifier 216M acts as well known in the art, amplifying a difference voltage between the non-inverting input 216P and the inverting input 216N. As the operational amplifier 216M is fed back, the output is controlled by the operational amplifier 216M such that the input voltage becomes at least essentially zero.

Resulting therefrom, for example provided that the first coupling element 216E and the second coupling element 216H both are resistors, which is preferred, and the reference potential being ground, a cutoff frequency of $1/(2\pi RC)$ and/or an amplification of $R_2/R_1$ is/are realized, where $R_2$ is the resistance of a second coupling element 216H, is the capacitance of capacitor 216G, and $R_1$ is the resistance of the first coupling element 216E.

In the alternative embodiment according to FIG. 13, the electrical filter 216F is realized passively, i.e. without active electronic devices. Again, the sensor electrode 217 is coupled with a discharge path 216C realized via the first coupling element 216E and, preferably, the second coupling element 216H to the reference potential 216D, for example ground. Further, the first coupling element 216E together with a charge carrier storage/capacitor 216G realizes the low path filter function of the electrical filter 216F which in addition might be influenced by the second coupling element 216H.

An additional amplifier 216R amplifying the filtered course of the electrode potential 217A can optionally be provided and is in FIG. 13, thus, depicted using dashed lines.

Referring to the discussion concerning FIG. 4 and the possibility of controlling the measuring arrangement 223, preferably regarding its gain 523 and/or with calibration information 521, in the example shown in FIG. 12 the AC source 216B or at least one of the first coupling element 216E and the second coupling element 216H can be variable and controlled accordingly. Referring to the second embodiment of FIG. 13, the AC source 216B and/or the amplifier 216R can be controlled. Further, in the embodiment of FIG. 12 an additional amplifier 216R can be provided as well at the same position as indicated in FIG. 13 (not shown) which might or might not be controllable as discussed with referring to FIG. 4.

The discharge path 216C and/or the electrical filter 216F outputs an output signal 216Q, which preferably is an analog signal being indicative of the capacitance value of the sensor electrode 217S.

The output signal 216Q preferably can optionally be digitalized by means of an A/D converter 224 and/or can be analyzed using the control interface 226 like previously discussed or differently.

For further details of control based on or taking into account detection of identification of a content or content change of the sensor portion 116 by means of the fluid sensor 206A, reference is made to the previous discussion as well.

In the following, the function of the fluid sensor 206A is discussed in further detail, additionally referring to FIGS. 14 and 15.

Figure 14:
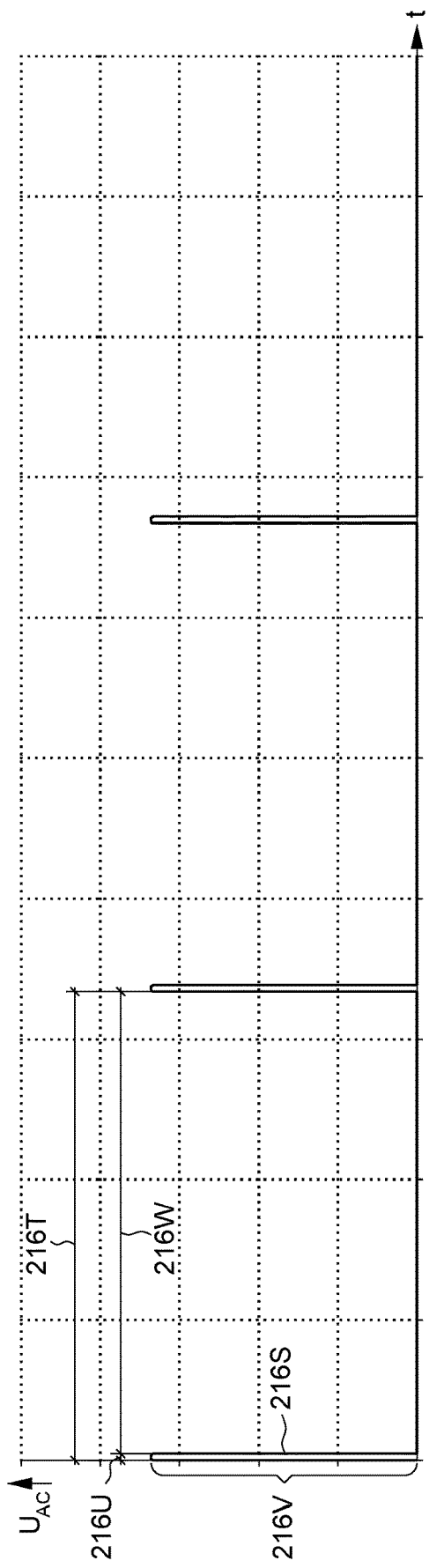
FIG. 14 is a diagram showing the output of the AC source and the electrode potential over time.
Figure 14:
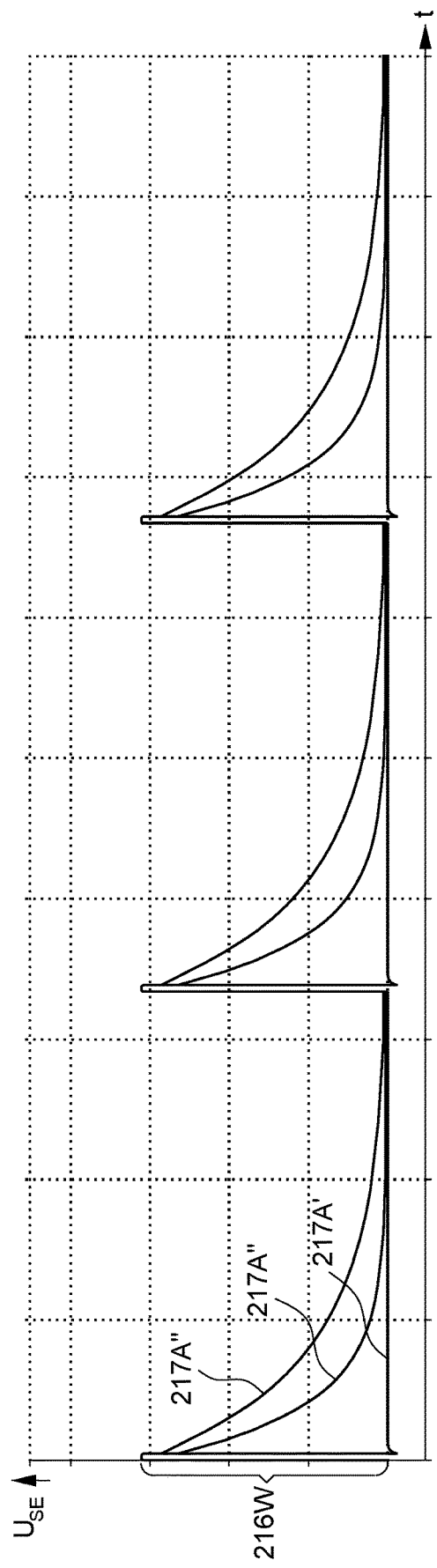

FIG. 14 shows in a first (upper) diagram a sequence 216S which can be provided by the AC source 216B to the UED 216A. In particular, the sequence 216S complies with an output voltage $U_{AC}$ of the AC source 216B.

Preferably, the AC source 216B is a pulse source. Accordingly, the first diagram of FIG. 14 shows a periodical signal with a period duration 216T including a pulse width 216U having an amplitude 216V, preferably followed by a delay phase, where the AC source 216B provides a reference potential, in the example shown ground, to the UED 216A.

In the example shown, the AC source 216B provides a pulse sequence with multiple periods. The pulse width 216U preferably is much shorter than the period 216T, in particular the pulse width 216U is less than 50%, more preferably less than 40%, 30% or 20% or less of the period 216D.

As shown in the first diagram of FIG. 14, the sequence 216S preferably is a square-pulse-sequence. However, alternatively or additionally the pulse form can be different, for example in shape of a sine half-wave, a trapezoidal pulse, a triangular pulse or the like.

The lower diagram in FIG. 14 shows the electrode potential 217A over time using the same time scale as used in the upper diagram showing the AC source 216B output.

As shown in FIG. 13, the AC source 216B charges the sensor electrode 217 via the UED 216A. The UED 216A might or in case the UED 216A is a diode does cause a voltage drop between the output of the AC source 216B and the sensor electrode 217. Thus, the electrode potential 217A might follow the output potential or output voltage of the AC source 216B depicted in the upper diagram of FIG. 14 apart from a potential voltage drop caused by the UED 216A, in particular a diode forward voltage if the UED 216A is realized by a diode.

Accordingly, the sensor electrode 207 is charged with the AC source 216B via the UED 216A to a pre-defined electrode potential 217A. This pre-defined electrode potential 217A preferably depends on the amplitude 216V of the AC source 216B provides.

Afterwards, the sensor electrode 207 is automatically discharged by means of the discharge path 216C starting from the pre-defined electrode potential 217A and approximating the electrode potential 217A to the reference potential 216D. In the embodiment of FIG. 12 the reference potential 217A is that of the node 216K which is directly connected with the non-inverting input 216P of the operational amplifier 216M as the operational amplifier 216M controls it accordingly. In the other embodiment shown in FIG. 13, the reference potential 216D is ground but can alternatively be set to a different potential if desired or required by further components of the fluid sensor 206A and/or evaluation electronics 216.

Provided that the discharge path 216C remains unchanged, the discharge curve of the sensor electrode 217 is different depending on the capacity value of the sensor electrode 217 and, thus, depending on the content or content change in the sensor portion 116 if the fluid sensor 206A is arranged in proximity to it. The lower diagram in FIG. 14 shows the development of the electrode potential 217A in three examples, namely a discharge curve 217A' with a minimum capacitance value, a second discharge curve 217A'' resulting from a higher capacitance value and a third discharge curve 217A''' resulting from an even higher capacitance value of the sensor electrode 217. Thus, the discharge curve shape and behavior depend on the capacitance value and, thus, on the content of the sensor portion 116 (the permittivity of the content of the sensor portion 116). Thus, the discharge curve 217A', 217A'', 217A''' can, and preferably is used to determine an indicator for the capacitance value and/or for the content change.

Figure 15:
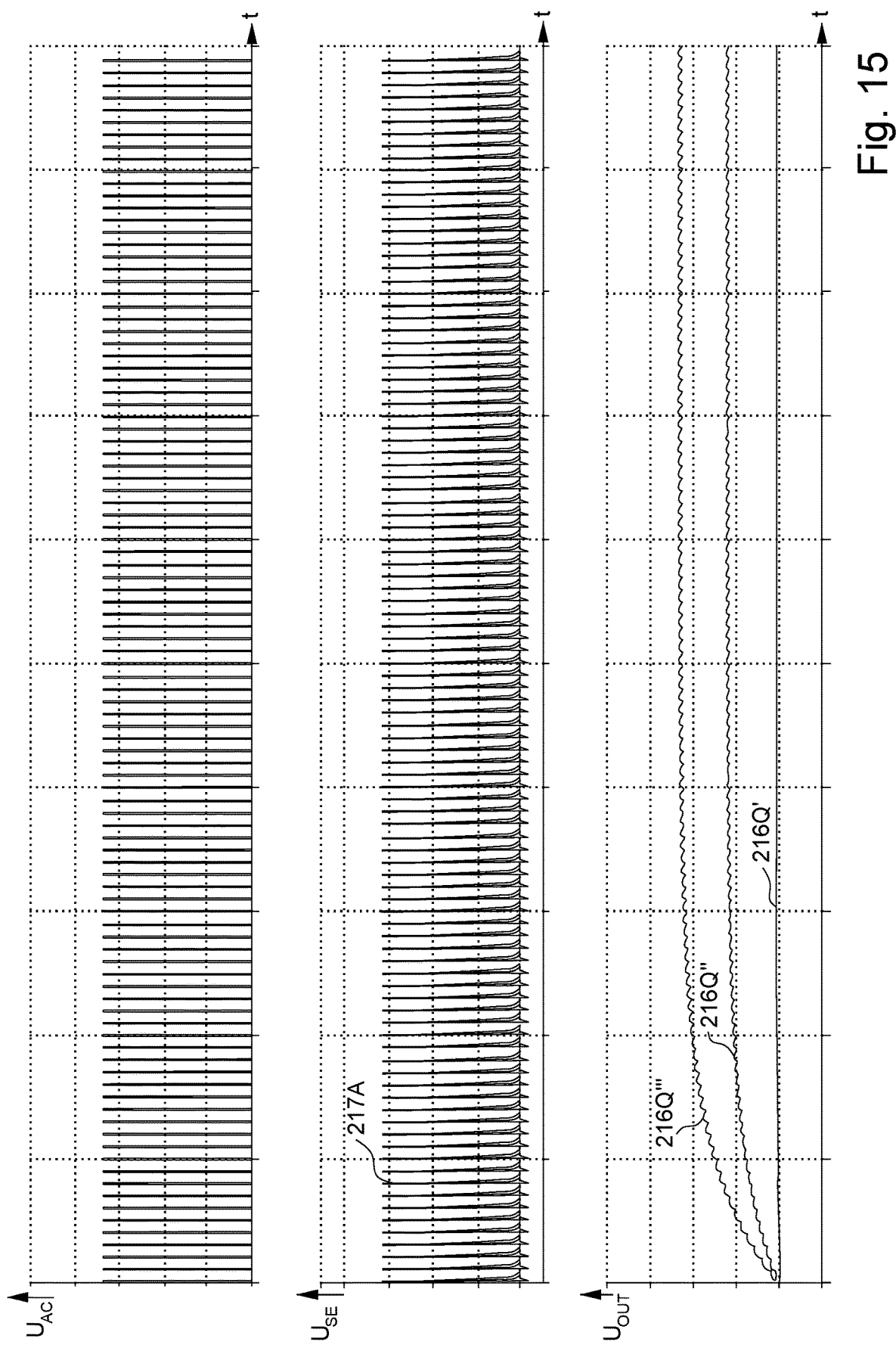
FIG. 15 is a diagram showing the output signal of the AC source, the electrode potential resulting therefrom, and a filtered sensor potential over time.

It is particularly preferred that the fluid sensor 206A repeatedly charges the sensor electrode 217 and discharges it afterwards by means of the discharge path 216C as depicted in FIG. 14 showing three periods 216T of the sequence 216S which is a section of the top diagram of FIG. 15 showing a multiplicity of periods 216T, and the resulting discharge curves 217A', 217A'', 217A''' with the same timescale in the second diagram of FIG. 15.

The fluid sensor 206A preferably forms the output signal 216Q based on a course of the electrode potential 217A during the course of discharge, the output signal 216Q being or forming basis for a measurement result 706A which is indicative of the capacitance value of the sensor electrode 217.

Preferably, the course of the electrode potential 217A is low path filtered, smoothened and/or integrated (at least to some extend) resulting in the output signal 216Q', 216Q'', 216Q''' based on discharge curves 217A', 217A'', 217A''', respectively. As can be seen in the lower diagram in FIG. 15 the output signal 216Q, apart from a remaining ripple, converges to a particular potential or voltage, which can also be referred to as offset voltage of the output signal 216Q depending on and, thus, being indicative of the capacitance value of the sensor electrode 217. Thus, the offset of said output signal 216Q is or can be examined to detect a particular capacitance value or change of the capacitance value of the sensor electrode 217. This further can be used to detect the content change.

The output signal 216Q can form the measurement result 706A as discussed referring to FIG. 4. In particular, as shown in FIG. 4 and as options shown in FIGS. 12 and 13 using dashed lines, the output signal 216Q can be digitalized using an A/D converter 224 and/or can be interpreted to detect the content change with the detection apparatus 225.

For example, the output signal level 216Q can be compared to a reference value or a change in the output signal level 216Q can be detected in order to identify a content change.

The process for generating the output signal 216Q might be a permanent continuous process resulting in a output signal level being at least essentially (apart from a ripple or other disturbances) unchanged until the content changes which causes the output signal 216Q to change, in particular drift away and preferably to increase or which can be detected and interpreted as a content change.

The output signal 216Q in the embodiment shown is formed by the electrical filter 216F and/or the discharge path 216C. The capacitance value of the sensor electrode 217 together with the discharge path 216C and/or the electrical filter 216F preferably results in a discharge time constant $\tau$.

The time constant $\tau$ in a rough approximation can be determined by multiplication of the capacitance value of the sensor electrode 217C and the resistance of the first coupling element 216E in case of the example depicted in FIG. 12 or the sum of the resistances caused by the first coupling element 216E and the second coupling element 216H in the example depicted in FIG. 13.

Alternatively, or additionally, the time constant $\tau$ can be determined graphically by determining time constant $\tau$ as the time difference $\tau=(a)-(b)$ between (a) and (b), where:

(a) is a time where an imaginary tangent intersects the level of reference potential 216D, in particular ground, wherein the imaginary tangent being tangent to the discharge path 216C at the time when the current flow from the AC source 216B stops and/or the pulse of the AC source 216B ends, and (b) is a time when the current flow from the AC source 216B stops and/or the pulse of the AC source 216B ends.

The period 216T preferably is chosen such that it is more than one $\tau$, preferably more than two or three $\tau$, and/or less than 20$\tau$, preferably less than 15, 10 or 5$\tau$.

As $\tau$ depends on whether the capacitance value with or without content in the sensor portion 116 is taken into account, the above preferably applies for the sensor portion 116 being filled with pure water or the expectable sample P.

A measurement process can particularly be summed up and the fluid sensor 206A or the evaluation electronics 216 can be arranged to perform the process as follows:

A very short pulse with a voltage $U_{AC}$ (amplitude) is applied to the UED (diode) 216A which will cause the sensor electrode 217 (the node 216I) to be fully charged to a sensor electrode voltage $U_{SE}=U_{AC}-V_D$ or to a corresponding electrode potential 217A. $V_D$ preferably is a forward voltage of the diode 216A.

The first coupling element (resistor) 216E in combination with the short pulse will not allow the capacitor 216G to be significantly charged.

That is, the first coupling element 216E and the capacitor 216G preferably are configured such that the pulse is able to charge the capacitor 216G only marginally, for example less than 20%, preferably 10%, particularly 5%.

The capacitor 216G can be called integrating capacitor as is at least to some extend integrates the electrode potential 217A and/or sensor voltage $U_{SE}$. Integration in this regard is understood broadly and preferably covers any kind of integration or accumulation or function which is or depends on an area beneath a track of the potential 217A and/or sensor voltage $U_{SE}$.

A period of $U_{AC}=0V$ follows which is long compared to the pulse. In this period the charge that has been stored in the sensor electrode 217 will flow through the first coupling element 216E and will be shared with the capacitor 216G causing its potential to increase.

A small portion of the charge will flow through the second coupling element 216H to GND (ground).

Thus, the second coupling element 216H is configured such that only such small portion of the charge flowing through the first coupling element 215E to the capacitor 216G will flow through the second coupling element 216H to GND (ground). The amount of charge that flows to the capacitor 216G and consequently the increase of the voltage can be proportional to the capacitance of the sensor electrode 217.

With the next pulse or further pulses, this process discussed under 1 to 4 is repeated. With increased voltage on the capacitor 216G and the second coupling element 216H more charge flows to GND (ground) through the second coupling element 216H. In particular, the voltage or potential at the capacitor 216G or node 216J increases causing more charge to flow to GND (ground) through the second coupling element 216H.

At a certain point, the amount of charge transferred from the sensor electrode 217 through the first coupling element 216E to the capacitor 216G will be equal to the amount of charge that flows through the second coupling element 216H to GND (ground). In this case we will have an equilibrium where the output voltage $U_{OUT}$ or corresponding potential at the second coupling element 216H, the capacitor 216G and/or output 216O, will stay at least essentially constant—regardless of a potentially remaining ripple or when averaged over a period.

The sensor electronics 216 can be configured such that a variation of less than 10% of output voltage $U_{OUT}$—regardless of a potentially remaining ripple or when averaged over a period—is realized within less than 100, preferably less than 50 or 30 periods. The period can have more than 10 µs and/or less than 1000 µs, preferably about 100 µs. Those values might be subject to change depending on the field of application.

The capacitor 216G preferably has a capacitance value such that at least three, preferably 10 periods are required to reach the equilibrium. Alternatively, or additionally, the capacitance value of the capacitor 216G preferably is higher than the capacitance value of the sensor electrode 217. In particular, the capacitance value of the capacitor 216G is more than two and/or less than 50 or 20 times the capacitance of the sensor electrode 217 in its operating position and with empty or gas filled sensor portion 116.

The capacitance value of the sensor electrode 217 preferably is less than the capacitance value of the capacitor 216G The potential at the second coupling element 216H, the capacitor 216G and/or output 216O can and optionally is buffered through amplifier 216R to form the output voltage $U_{OUT}$.

The resistance of the second coupling element 216H divided by the resistance of the first coupling element 216E preferably is more than 5 and/or less than 20. The resistances might be in the megohm range. The capacitor 216G might have a capacitance value in the nF range. Those preferred exemplary values are subject to changes depending on the field of application.

The buffer amplifier 216R preferably is positioned directly besides the sensor electrode 217, evaluation electronics 216 and/or fluid sensor 206A and might form part of the latter. This helps improving a reliable measurement avoiding distortions.

Individual aspects and features of the present invention and individual method steps and/or method variants may be implemented independently from one another, but also in any desired combination and/or order.

In particular, the present invention relates also to any one of the following aspects which can be realized independently or in any combination, also in combination with any aspects described above or in the claims:

1. Fluid sensor 206A for detecting a content change, in particular a liquid front PF1, PF2, in a sensor portion 116 of a fluid system 103,
    wherein the fluid sensor 206A includes at least one sensor electrode 217, the sensor electrode 217 having an electrode potential 217A and a capacitive behavior, the sensor electrode 217 thus being capable to store electrical energy in an electrical field 217B formed by the sensor electrode 217 when being charged causing the electrode potential 217A to change accordingly,
    wherein a capacitance value of the sensor electrode 217 varies when the content changes,
    wherein the fluid sensor 206A includes evaluation electronics 216, the evaluation electronics 216 including a unidirectional electrical device 216A, in the following referred to as UED 216A, and an AC source 216B,
    wherein the AC source 216B is coupled via the UED 216A to the sensor electrode 217 to charge the sensor electrode 217, and
    wherein the evaluation electronics 216 includes a discharge path 216C coupled to the sensor electrode 217 for discharging the sensor electrode 206A, and/or an energy storage, in particular capacitor 216G, coupled to the sensor electrode such that charge from the sensor electrode 217 is shareable with said energy storage.
2. The fluid sensor according to aspect 1, characterized in that the UED 216A is configured to enable charging the sensor electrode 207 via the UED 216A while the UED 216A is configured to block discharging the sensor electrode 207 via the UED 216A.
3. The fluid sensor according to aspect 1 or 2, characterized in that the discharge path 216C couples the sensor electrode 207 with a reference potential 216D via at least a first coupling element 216E such that the sensor electrode 207 is continuously charged or discharged when the electrode potential 217A differs from the reference potential 216D causing the electrode potential 217A to approximate the reference potential 216D.
4. The fluid sensor according to any one of the preceding aspects, characterized in that the fluid sensor 206A includes an electrical filter 216F, the electrical filter 216F preferably being a low pass filter and/or configured to smoothen the course of the electrode potential 217A, the electrical filter 216F being electrically coupled with the sensor electrode 207 and being configured to form a measurement result 206A based on the course of the electrode potential 217A.
5. The fluid sensor according to aspects 3 and 4, characterized in that the electrical filter 216F includes a capacitor 216G, wherein the capacitor 216G is electrically coupled to the sensor electrode 217 via the first coupling element 216E of the discharge path 216C.
6. The fluid sensor according to aspect 5, characterized in that the discharge path 216C includes a second coupling element 216H being coupled in a common node 216J with the capacitor 216G and the first coupling element 216E, the second coupling element 216H coupling the first coupling element 216) with a reference node (216K) which is at reference potential 216D.

7. The fluid sensor according to aspect 6, characterized in that the first coupling element 216E and/or second coupling element 216H is or are a resistor, that the UED 216A is a diode, and/or that the AC source 216B is a pulse source.

8. The fluid sensor according to any one of aspects 5 to 7, characterized in that the electrical filter 216F is an active filter including an operational amplifier 216M, preferably forming a measuring arrangement 223, wherein an inverting input 216N of the operational amplifier 216M is coupled with the sensor electrode 217 via the first coupling element 216E, wherein an output 216O of the operational amplifier 216M is fed back to the inverting input 216N via the capacitor 216G and the second coupling element 216H connected in parallel, and wherein the reference potential 216D is provided to a non-inverting input 216P of the operational amplifier 216M.

9. The fluid sensor according to any one of aspects 5 to 7, characterized in that the electrical filter 216F is a passive filter, wherein the sensor electrode 217 is coupled via the first coupling element 216E to the capacitor 216G and the second coupling element 216H, the second connecting element 216H connecting the first coupling element 216E to the reference potential 216D.

10. The fluid sensor according to any one of the preceding aspects, characterized in that the fluid sensor 206A is configured to repeatedly charge the sensor electrode 207 with the AC source 216B via the UED 216A to a predefined electrode potential 217A and to automatically discharge the sensor electrode 207 by means of the discharge path 216C starting from the predefined electrode potential 217A approximating the electrode potential 217A to the reference potential 216D each time after charging is finished.

11. The fluid sensor according aspect 10, characterized in that the fluid sensor 206A is configured to form an output signal 216Q based on a course of the electrode potential 217A during the course of discharge, the output signal 216Q being or forming a basis for a measurement result 706A which is indicative of the capacitance value of the sensor electrode 217 or of the content change.

12. The fluid sensor according to any one of the preceding aspects, characterized in that the fluid sensor 206A includes a counter electrode 217C in a common plane 217D with the sensor electrode 217, the sensor electrode 217 and the counter electrode 217C being configured to be arranged close to the sensor portion 116 such that a content change is detectable by means of change in capacity formed between the sensor electrode 217 and the counter electrode 217C.

13. The fluid sensor according to aspect 12, characterized in that the sensor electrode 217 is connected via a sensor line 218 having a shield electrode 219, the shield electrode 219 causing a constant known capacity between the shield electrode 219 and the sensor electrode 217.

14. Analysis system 1 for testing an in particular biological sample B, the analysis system 1 including an analysis device 200 for receiving a cartridge 100 including a fluid system 103 having a sensor portion 116, the analysis device 200 including a fluid sensor 206A according to any one of the proceeding aspects for detecting a content change, in particular a liquid font PF1, PF2, in the sensor portion 116.

15. Process for detecting a content change, in particular a liquid front PF1, PF2, in a sensor portion 116 of a fluid system 103 with a fluid sensor 206A according to any one of the preceding aspects, wherein the evaluation electronics 216 of the fluid sensor 206A repeatedly charges the sensor electrode 207 with the AC source 216B via the UED 216A to a predefined electrode potential 217A and automatically discharges the sensor electrode 207 by means of the discharge path 216C starting from the predefined electrode potential 217A approximating the electrode potential 217A to the reference potential 216D and/or sharing charge of the sensor electrode 217 with an energy storage each time after charging is finished, preferably wherein the fluid sensor 206A forms an output signal 216Q based on a course of the electrode potential 217A during the course of discharge, the output signal 216Q being or forming a basis for a measurement result 706A which is indicative of the capacitance value of the sensor electrode 217.

What is claimed is:

1. A fluid sensor for detecting a content change in a sensor portion of a fluid system, comprising:
    at least one sensor electrode, responsive to a content change of a fluid system with which the sensor portion is associated, the sensor electrode having an electrode potential and a capacitive behavior, the sensor electrode adapted to store electrical energy in an electrical field formed by the sensor electrode when being charged to cause the electrode potential to change accordingly, wherein a capacitance value of the sensor electrode varies when the content changes; and
    evaluation electronics for detecting a change in electrical properties of the sensor portion when a content change of the fluid system takes place using the sensor electrode, the evaluation electronics including a unidirectional electrical device (UED), and an AC source,
    wherein the AC source is coupled via the UED to the sensor electrode to charge the sensor electrode, and
    wherein the evaluation electronics includes a discharge path coupled to the sensor electrode for discharging the sensor electrode through a lowpass filter to output the content change, and an energy storage coupled to the sensor electrode such that charge from the sensor electrode is shareable with said energy storage.

2. The fluid sensor according to claim 1, wherein the UED is configured to enable charging the sensor electrode via the UED, and the UED is configured to block discharging of the sensor electrode via the UED.

3. The fluid sensor according to claim 1, wherein the discharge path couples the sensor electrode with a reference potential via a first coupling element such that the sensor electrode is continuously charged or discharged when the electrode potential differs from the reference potential thereby causing the electrode potential to approximate the reference potential.

4. The fluid sensor according to claim 3, wherein the first coupling element is a resistor or a device having an impedance where the ohmic resistance forms the major part.

5. The fluid sensor according to claim 3, wherein second coupling element is a resistor or a device having an impedance where the ohmic resistance forms a major part.

6. The fluid sensor according to claim 1, wherein the low pass filter comprises an electrical filter electrically coupled with the sensor electrode and configured to form a measurement result based on a course of the electrode potential.

7. The fluid sensor according to claim 6, wherein the electrical filter comprises a capacitor, wherein the capacitor is electrically coupled to the sensor electrode via the first coupling element of the discharge path.

8. The fluid sensor according to claim 7, wherein the discharge path comprises a second coupling element being coupled in a common node with the capacitor and the first coupling element, the second coupling element coupling the first coupling element with a reference node which is at reference potential.

9. The fluid sensor according to claim 6, wherein the electrical filter is an active filter including an operational amplifier, wherein an inverting input of the operational amplifier is coupled with the sensor electrode via the first coupling element, wherein an output of the operational amplifier is fed back to the inverting input via the capacitor and the second coupling element connected in parallel, and wherein the reference potential is provided to a non-inverting input of the operational amplifier.

10. The fluid sensor according to claim 6, wherein the electrical filter is a passive filter, wherein the sensor electrode is coupled via the first coupling element to the capacitor and the second coupling element, the second coupling element connecting the first coupling element to the reference potential.

11. The fluid sensor according to claim 1, wherein the UED is a diode or a device behaving as a diode.

12. The fluid sensor according to claim 1, wherein the AC source is a pulse source.

13. The fluid sensor according to claim 1, wherein the fluid sensor is configured to repeatedly charge the sensor electrode with the AC source via the UED to a predefined electrode potential and to automatically discharge the sensor electrode through the discharge path starting from the predefined electrode potential approximating the electrode potential to the reference potential each time after charging is finished.

14. The fluid sensor according to claim 13, wherein the fluid sensor is configured to form an output signal based on a course of the electrode potential during the course of discharge, the output signal being or forming a basis for a measurement result which is indicative of the capacitance value of the sensor electrode or of the content change.

15. The fluid sensor according to claim 1, further comprising a counter electrode in a common plane with the sensor electrode, the sensor electrode and the counter electrode being arranged close to the sensor electrode such that a content change is detectable by means of change in capacity formed between the sensor electrode and the counter electrode.

16. The fluid sensor according to claim 15, wherein the sensor electrode is connected via a sensor line having a shield electrode, the shield electrode causing a constant known capacity between the shield electrode and the sensor electrode.

17. Analysis system for testing a biological sample, the analysis system comprising an analysis device for receiving a cartridge including a fluid system having a sensor portion, the analysis device including a fluid sensor for detecting a content change in a sensor portion responsive to a content change of a fluid system with which the sensor portion is associated, wherein the fluid sensor includes at least one sensor electrode, the sensor electrode having an electrode potential and a capacitive behavior, the sensor electrode configured to store electrical energy in an electrical field formed by the sensor electrode when being charged causing the electrode potential to change accordingly, wherein a capacitance value of the sensor electrode varies when the content changes, wherein the fluid sensor includes evaluation electronics for detecting a change in electrical properties of the sensor portion when a content change of the fluid system takes place using the sensor electrode, the evaluation electronics including a unidirectional electrical device, in the following referred to as UED, and an AC source, wherein the AC source is coupled via the UED to the sensor electrode to charge the sensor electrode, and wherein the evaluation electronics comprises a discharge path coupled to the sensor electrode for discharging the sensor electrode through a lowpass filter to output the content change and an energy storage coupled to the sensor electrode such that charge from the sensor electrode is shareable with said energy storage.

18. A process for detecting a content change in a sensor portion of a fluid system with a fluid sensor for detecting a content change in a sensor portion of a fluid system, wherein the fluid sensor includes at least one sensor electrode, the sensor electrode having an electrode potential and a capacitive behavior, the process comprising:

storing electrical energy in an electrical field formed by the sensor electrode when being charged causing the electrode potential to change accordingly, wherein a capacitance value of the sensor electrode varies when the content changes, wherein the fluid sensor includes evaluation electronics for detecting a change in electrical properties of the sensor portion when a content change of the fluid system takes place using the sensor electrode, the evaluation electronics including a unidirectional electrical device, in the following referred to as UED, and an AC source, wherein the AC source is coupled via the UED to the sensor electrode to charge the sensor electrode, wherein the evaluation electronics includes a discharge path coupled to the sensor electrode for discharging the sensor electrode through a lowpass filter to output the content change; and an energy storage coupled to the sensor electrode such that charge from the sensor electrode is shareable with said energy storage, and wherein the evaluation electronics of the fluid sensor repeatedly charges the sensor electrode with the AC source via the UED to a predefined electrode potential and automatically discharges the sensor electrode by means of the discharge path starting from the predefined electrode potential approximating the electrode potential to the reference potential or sharing charge of the sensor electrode with an energy storage each time after charging is finished.

19. The process according to claim 18, further comprising forming an output signal based on a course of the electrode potential during a course of discharge, the output signal being or forming a basis for a measurement result which is indicative of the capacitance value of the sensor electrode.

* * * * *